United States Patent [19]

Hogrefe et al.

[11] Patent Number: 4,561,443
[45] Date of Patent: Dec. 31, 1985

[54] COHERENT INDUCTIVE COMMUNICATIONS LINK FOR BIOMEDICAL APPLICATIONS

[75] Inventors: Arthur F. Hogrefe, Laurel; Wade E. Radford, Columbia, both of Md.

[73] Assignee: The Johns Hopkins University, Baltimore, Md.

[21] Appl. No.: 473,248

[22] Filed: Mar. 8, 1983

[51] Int. Cl.$^4$ ............................................. A61N 1/36
[52] U.S. Cl. ...................... 128/419 PG; 128/419 PT; 128/903; 604/65
[58] Field of Search .................. 128/419 PG, 419 PT, 128/903; 604/65-67, 93, 95, 245, 49, 50; 370/9; 375/45, 118, 62; 455/41

[56] References Cited

U.S. PATENT DOCUMENTS

| | | | |
|---|---|---|---|
| 3,827,026 | 7/1974 | Viswanathan | 370/9 |
| 4,090,135 | 5/1978 | Farstad et al. | 455/41 |
| 4,107,459 | 8/1978 | Stamper | 375/118 |
| 4,223,679 | 9/1980 | Schulman et al. | 128/419 PT |
| 4,373,527 | 2/1983 | Fischell | 128/DIG. 12 |
| 4,390,022 | 6/1983 | Calfee et al. | 128/419 PG |
| 4,404,972 | 9/1983 | Gordon et al. | 128/419 PG |
| 4,441,210 | 4/1984 | Hochmair et al. | 455/41 |

Primary Examiner—Kyle L. Howell
Assistant Examiner—Ruth S. Smith
Attorney, Agent, or Firm—Robert E. Archibald; Howard W. Califano

[57] ABSTRACT

A two-way coherent inductive communications link between an external transceiver and an internal transceiver located in a biologically implanted programmable medical device. Digitally formatted command data and programming data is transmitted to the implanted medical device by frequency shift keying the inductive communications link. Internal transceiver is powered by the inductive field between internal and external transceivers. Digitally formatted data is transmitted to external transceiver by internal transceiver amplitude modulating inductive field. Immediate verification of the establishment of a reliable communications link is provided by determining existence of frequency lock and bit phase lock between internal and external transceivers.

20 Claims, 36 Drawing Figures

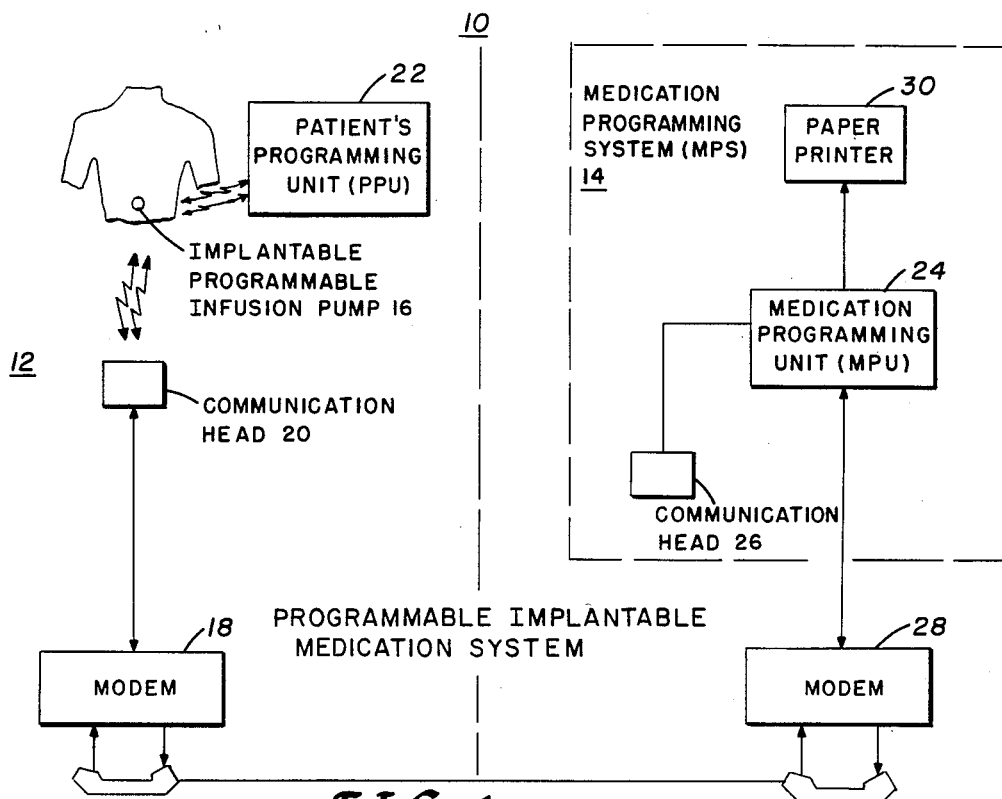
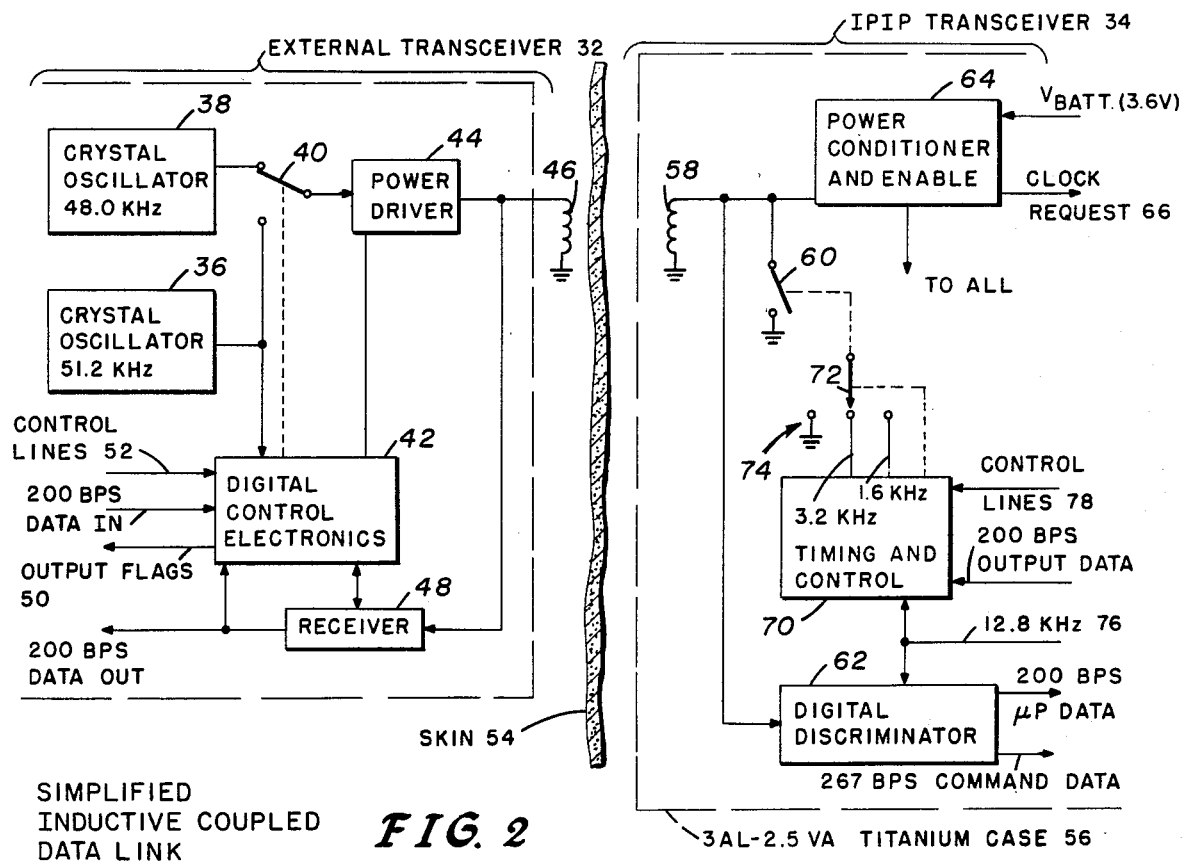
FIG. 1
FIG. 2
SIMPLIFIED INDUCTIVE COUPLED DATA LINK

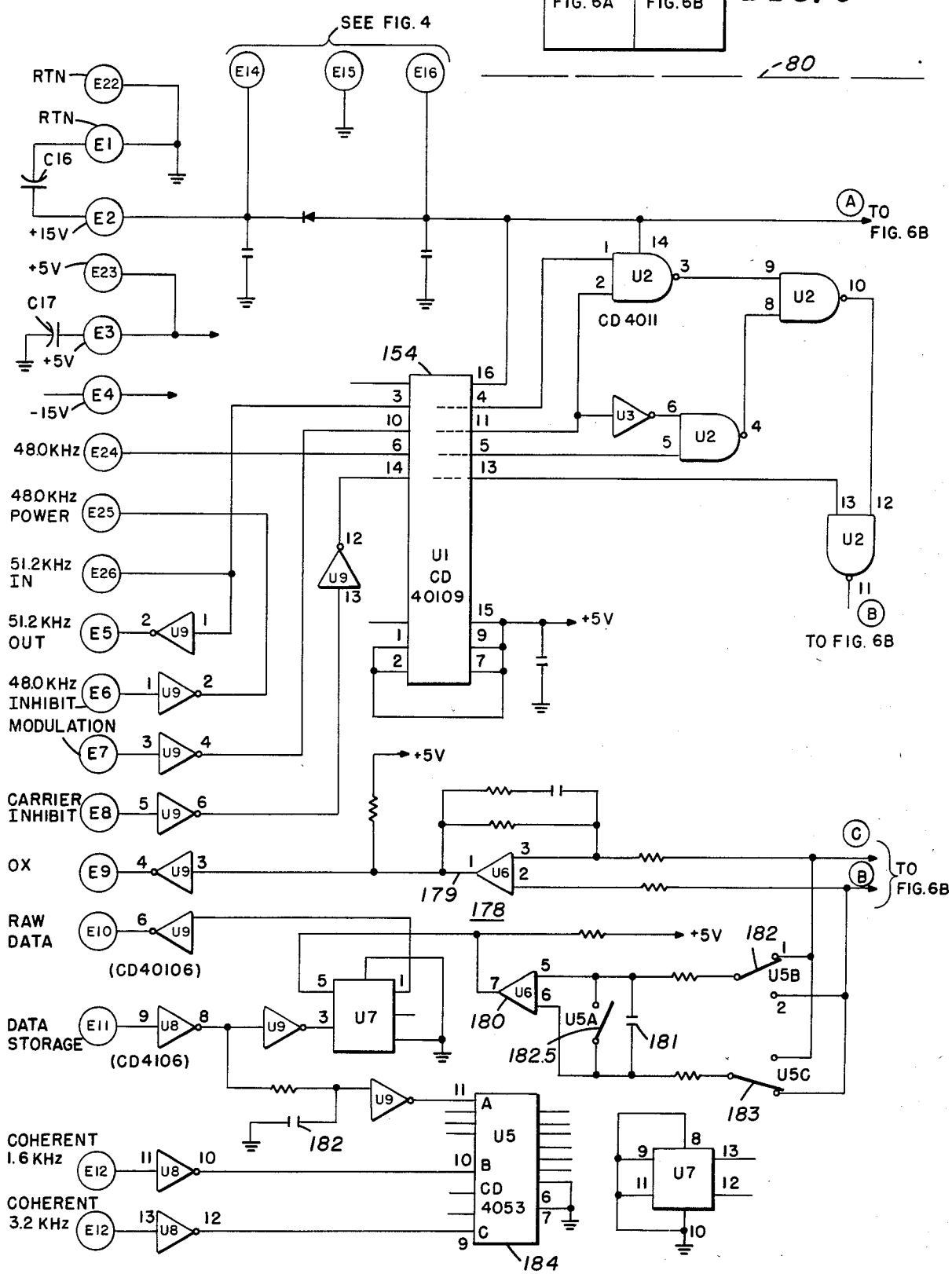
FIG. 6A — MPU CONTROL LOGIC AND SYNCHRONOUS DETECTOR

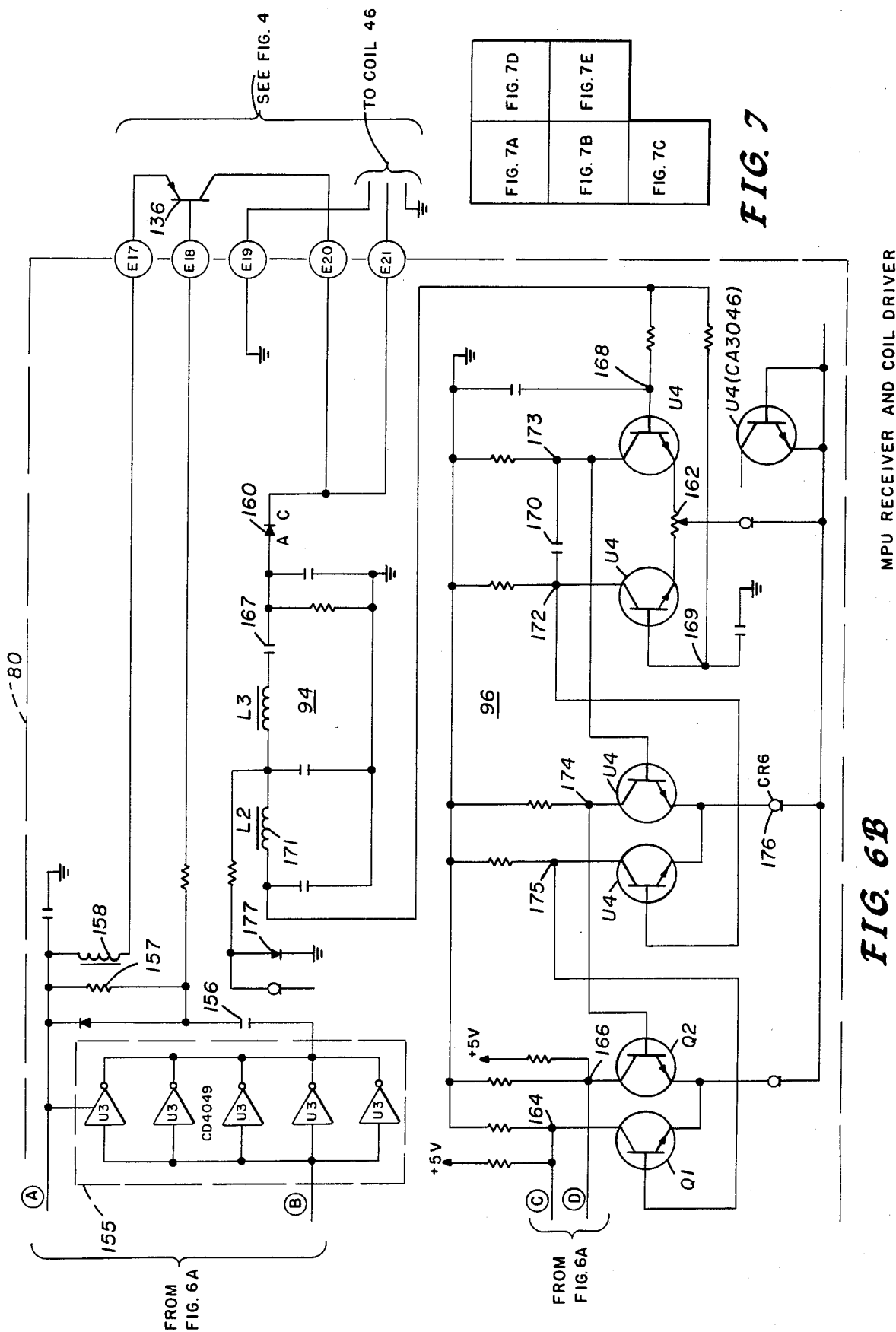

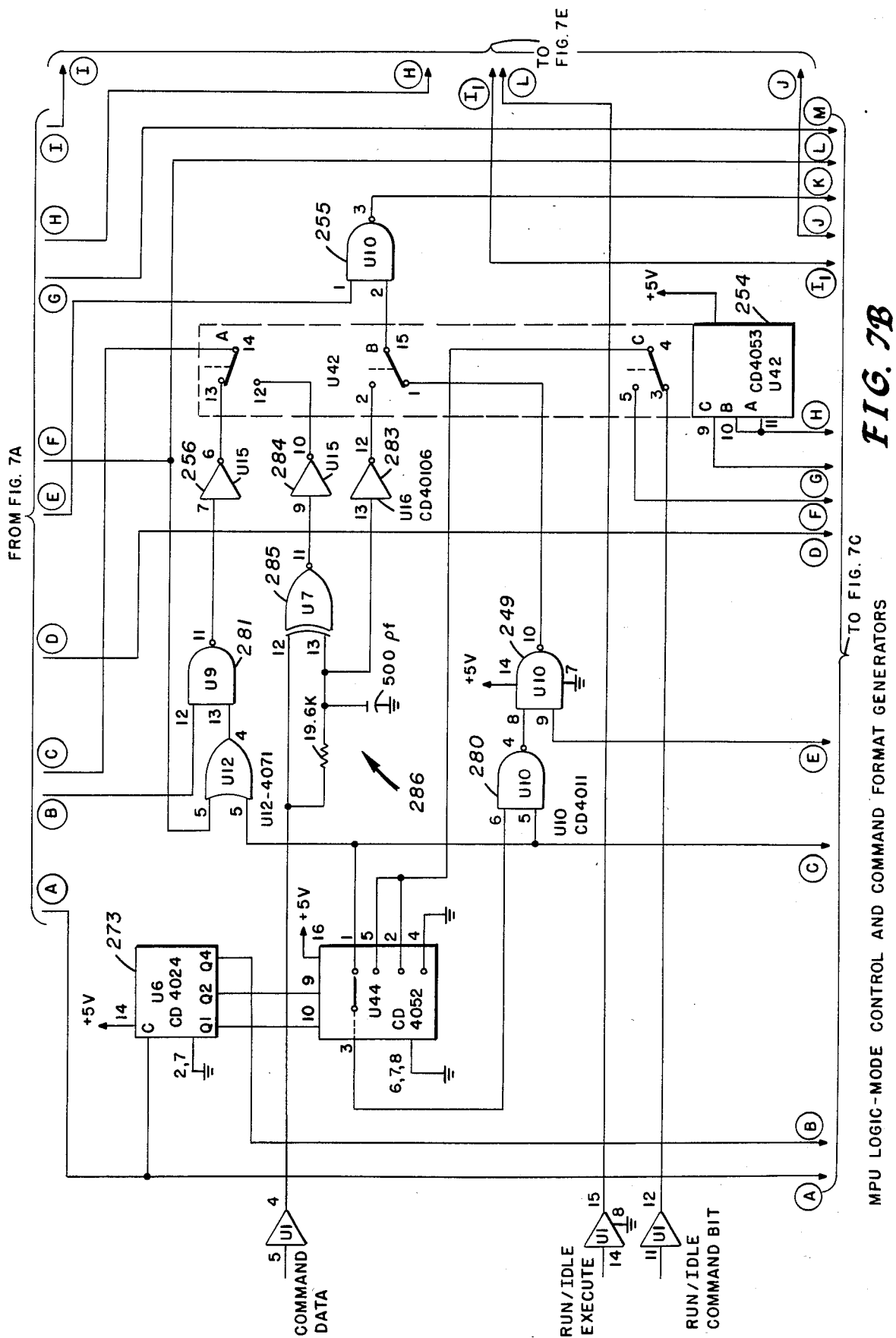

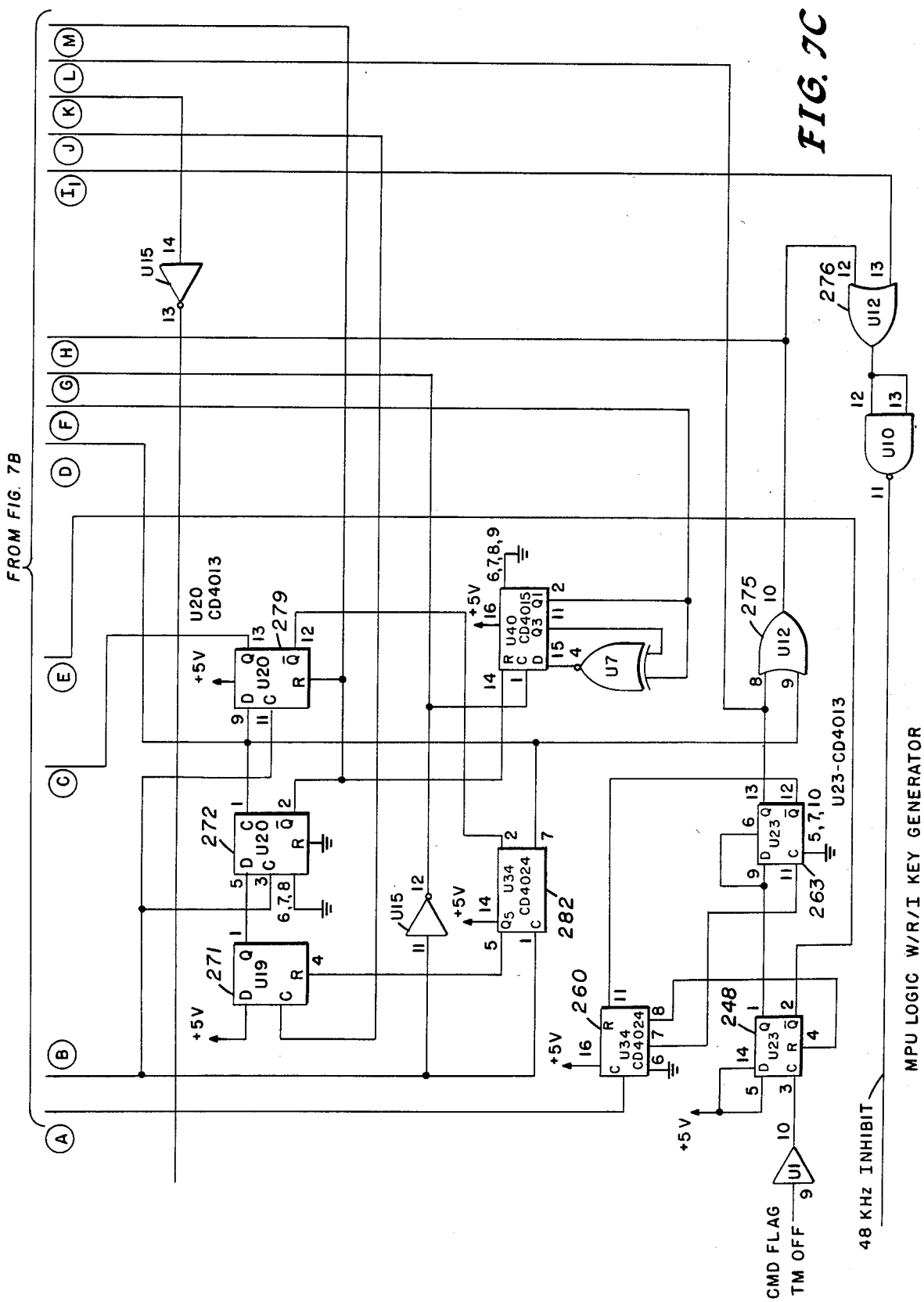

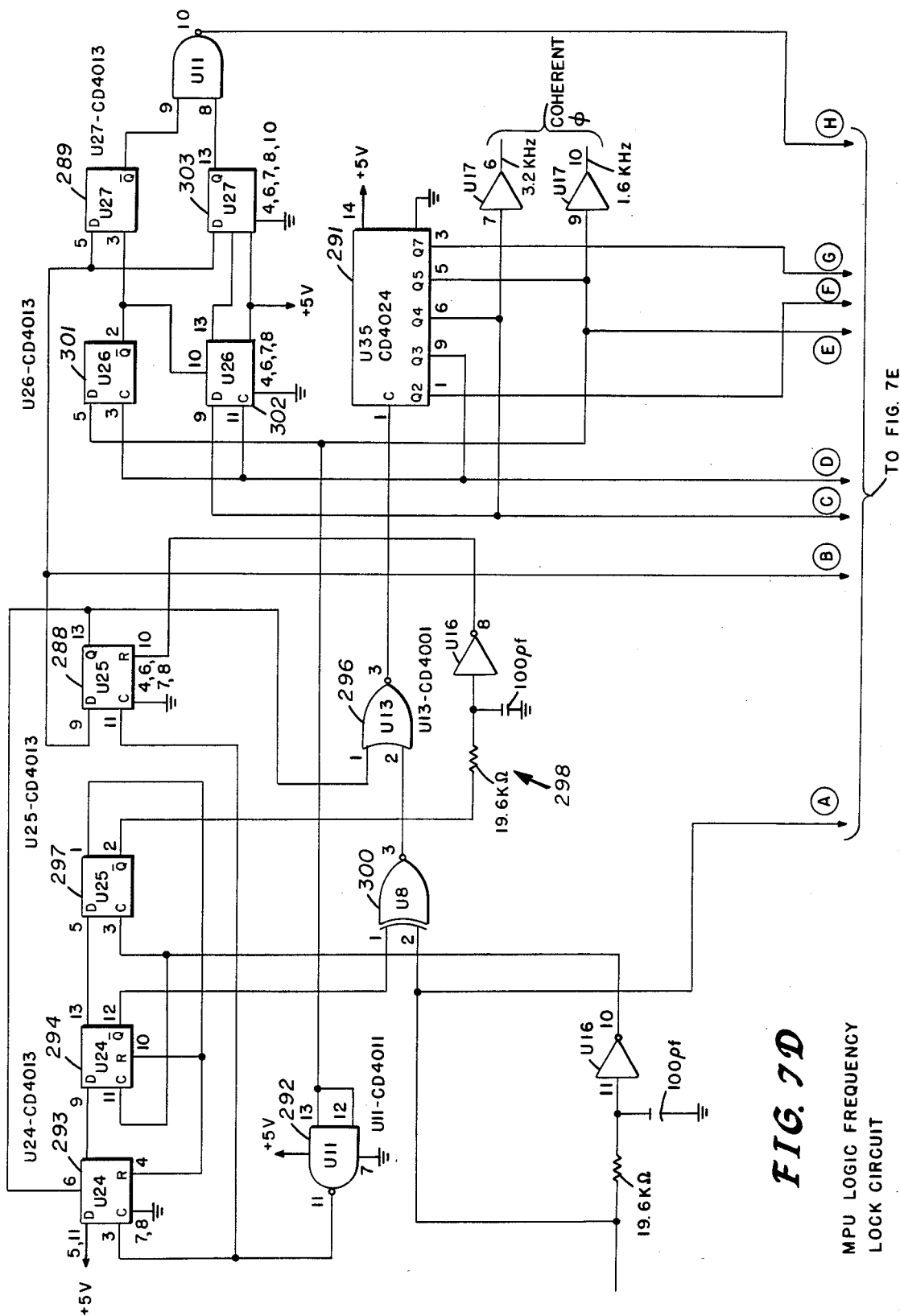
FIG. 7D  MPU LOGIC FREQUENCY LOCK CIRCUIT

MPU BIT LOCK CIRCUIT AND R/I COMMAND TM SYNC

IPIP TRANSCEIVER BLOCK DIAGRAM

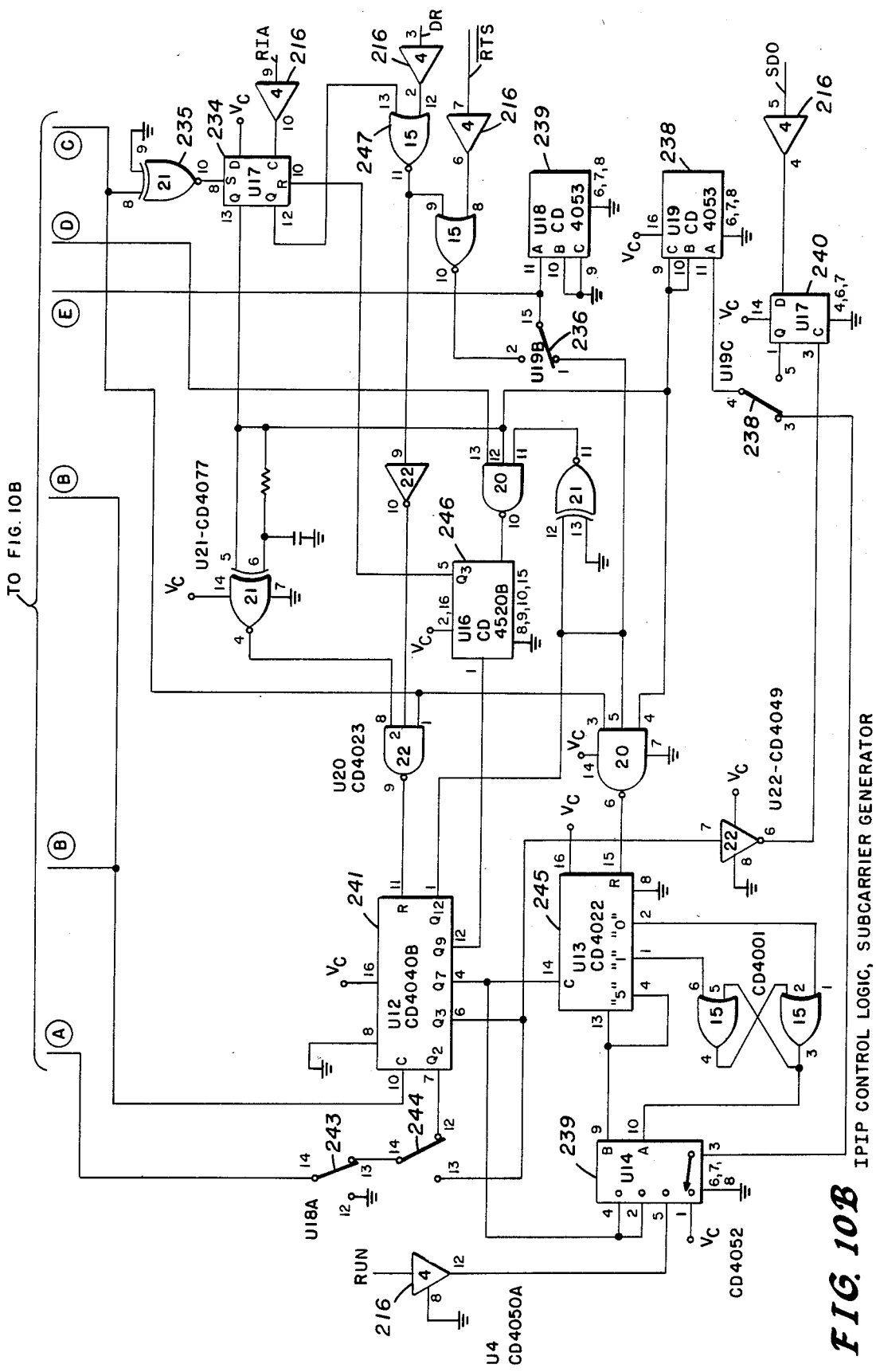

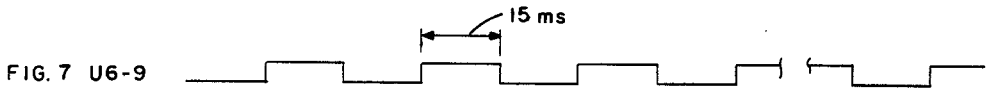
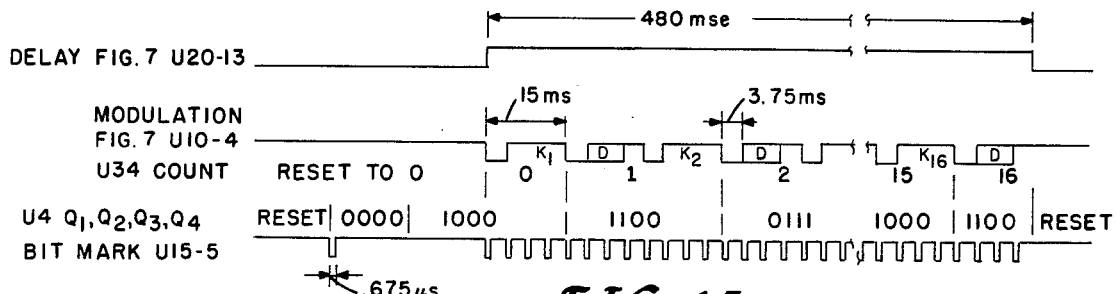
FIG. 15
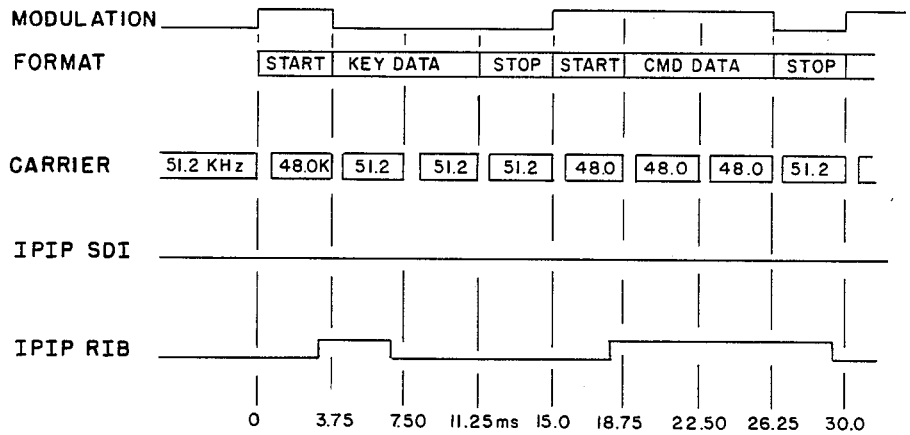
FIG. 16
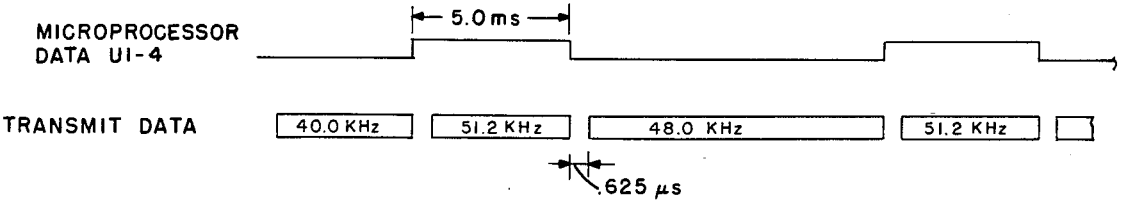
FIG. 17

PPU TRANSCEIVER BLOCK DIAGRAM

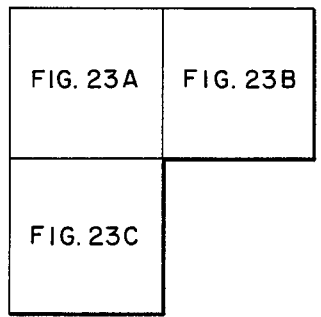
FIG. 23
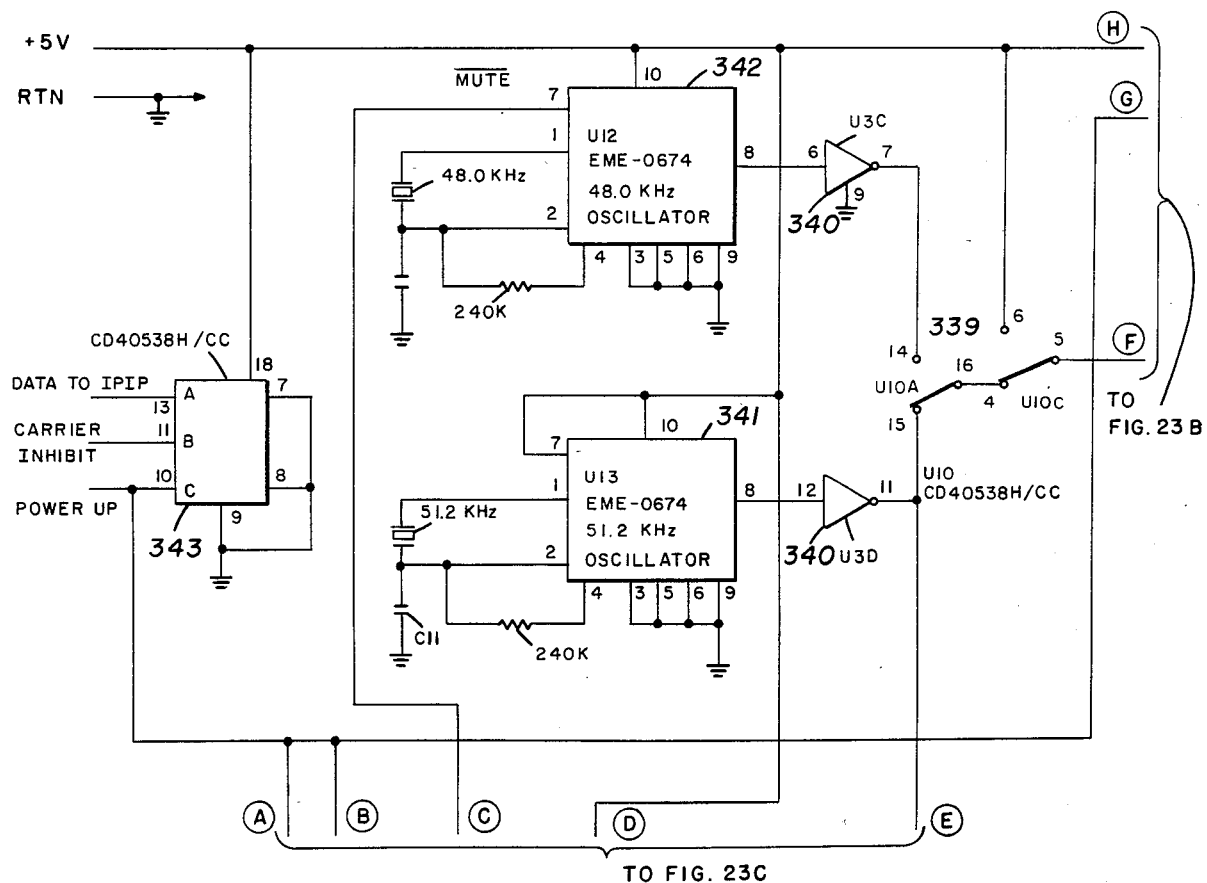
FIG. 23A        PPU CRYSTAL CONTROLLED OSCILLATORS

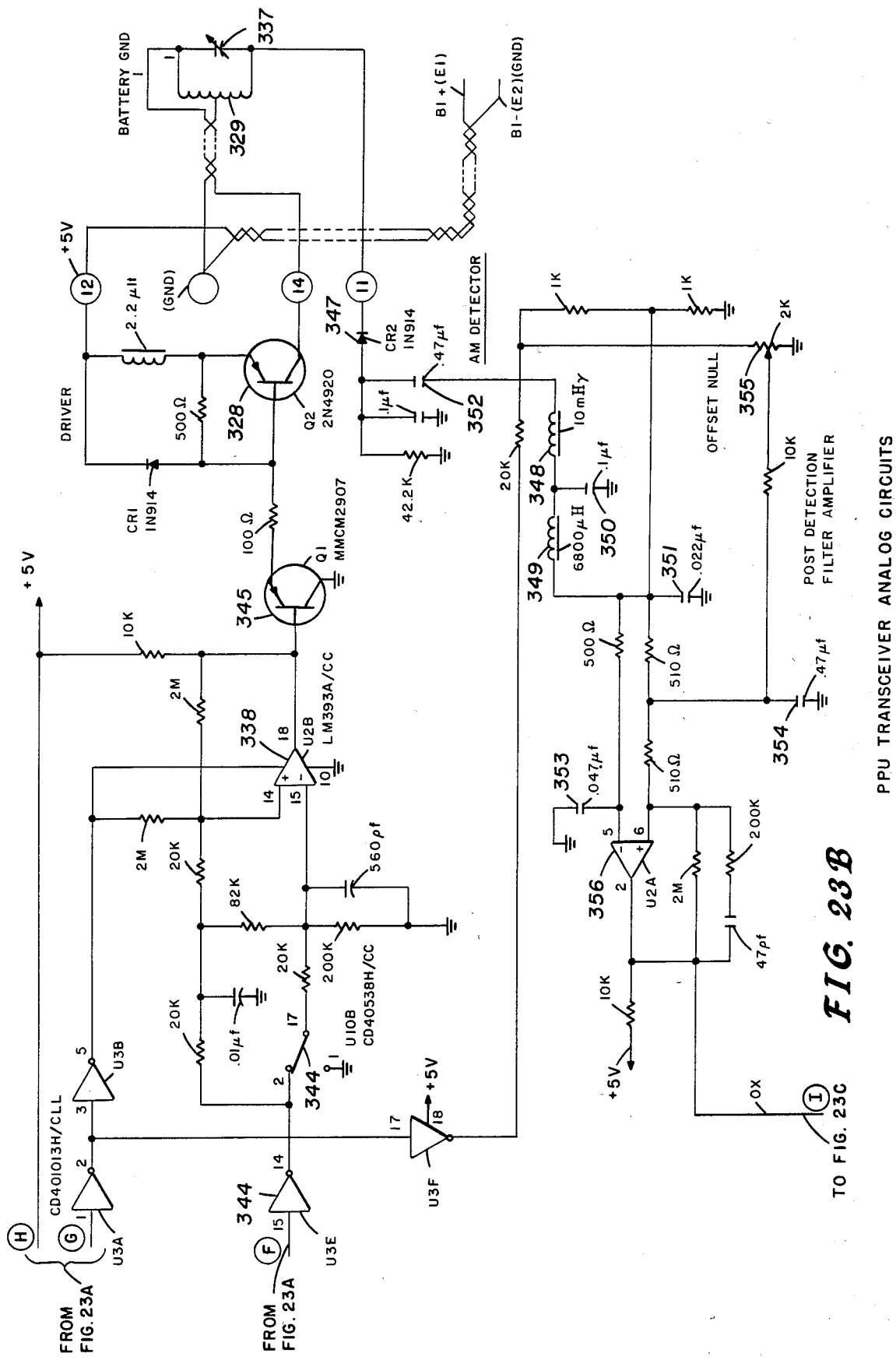

COHERENT INDUCTIVE COMMUNICATIONS LINK FOR BIOMEDICAL APPLICATIONS

STATEMENT OF GOVERNMENTAL INTEREST

The invention herein described was made in the performance of work under NASA Contract No. NDPR S-63983B and is subject to the provisions of Section 305 of the National Aeronautics and Space Act of 1958 (72 Stat. 435; 42 U.S.C. 2457).

BACKGROUND OF THE INVENTION

This invention relates generally to a means and method for communicating with a programmable biologically implanted medication system and more specifically to a means and method for establishing a coherent inductive communications link with a programmable biologically implanted medication system for transmitting commands to the implanted medication system and for receiving telemetry data from the implanted medication system.

An example of such a programmable implantable medication system is disclosed in U.S. Pat. No. 4,373,527 issued Feb. 15, 1983.

In the field of biologically implanted devices such as cardiac pacers and medication infusion pumps, efficiency and accuracy are the paramount concerns. As can be appreciated, an inaccurately programmed or controlled cardiac pacer could mean death to the patient. Likewise some medications being infused by an implanted infusion pump would be lethal if overdosed and would be ineffective if underdosed. The devices must also be efficient to prevent power failure and to preclude having to replace power supplies in the implanted device after short periods of time. In the field of implantable devices there has been an increased utilization of digital circuitry due to the advances made in digital technology. The advantages of digital circuitry correlate to the requirements of an implanted device, i.e., efficiency and accuracy of control. Initially cardiac pacers were simple analog devices which had performance reliability. With improvements in digital techniques and developing techniques for fabricating compact, low power digital circuitry, digital implanted devices, such as cardiac pacers, have become more popular. In addition, the development of much improved batteries has also encouraged the use of digital control techniques in implanted devices.

In nearly all of the devices that are implanted in the human body it is either absolutely necessary or highly desirable to have the ability to reprogram the operating parameters and to monitor the performance of the device, both historically and contemporaneously. To add flexibility to the use of implanted devices and to free the patient from restrictive close ties to a medical center, it is desirable that the implanted device be reprogrammable by the patient as well as the doctor and that the implanted device be reprogrammable by the doctor from a remote location. Because of the reprogrammability by the patient, the desirability and the necessity of having an historical record of the operation of the implanted device is increased.

The nature of some implanted devices is such that it is desirable to reprogram the operating characteristics very often. For example, with an insulin dispensing implanted device it may be necessary that the patient reprogram the implanted device after each meal or snack with data reflecting the size of the meal and the contents of the meal. This is necessary so that the insulin dispensing device dispenses insulin at a rate and profile closely matching a healthy pancreas. Because of the large number of reprogrammings it is necessary that the reprogramming procedure is accomplished with little or no power drain to the power supply in the implanted device.

As can be appreciated, the success of an implanted device with respect to their life sustaining purpose and their life threatening potential is highly dependent upon the ability to establish a reliable, accurate and verifiable communications link to and from the implanted device. The communications system must have the ability to rapidly establish reliable communications, communicate accurate command data and reprogramming data, verify the receipt of the communicated data by the implanted device and to communicate historical operational data from the implanted device. Because of the precision necessary in the administration of insulin, drugs, chemotherapeutic agents, etc., to the human, the communications link must be highly resistant or impervious to external extraneous noise. To decrease the probability of failure of the implanted device, which would require surgery to replace it, a system with as much complexity as possible residing in the external device must be provided. The implanted device must have the ability to accurately discriminate between command data and programming data. The system must have a method to confirm communications link integrity, verify transmitted data and advise of the operational status of the implanted device.

The prior art discloses various means and methods for communicating with an implanted device. The prior art also identifies a number of problems associated with reliably communicating control data to an implanted device. However, none of the known prior art provides all of the above-stated requirements for a reliable, accurate, verifiable communications link. In a number of the prior art systems, a programming signal must be converted by the implanted device into a proper logic form for control of the implanted device. In these devices it must be assumed, i.e., there is no direct verification, that the signal was accurately received by the implanted device. Another problem in a number of prior art devices is that accessing the implanted device is conducted independently of transmitting the control data. Absent means of verification, the result is that there is no control over ensuring accurate data input after access has been accomplished even though the implanted device may be reliably isolated from being reprogrammed by external, extraneous signals or interference in the communications link. Interference can cause either improper control data input or cause the implanted device to improperly decode the control data.

The U.S. Pat. No. 4,126,139 to Walters et al., entitled "Method and Means for Receiving Parameter Control Data in an Implantable Heart Pacer", discloses a heart pacer employing a digital parameter controlling circuit which is controlled by data received from an external source with the data in the form of magnetic pulses of a width corresponding to the desired logic state of the parameter controlling signal. The transmitted signal contains both parameter data for controlling selected pacer parameter operation and access data which is processed by the implanted pacer for determining whether the parameter data is accepted for control purposes. To attempt to ensure proper receipt of the parameter data it is intermixed with access data and certain selected bits of the resulting binary word are compared within the implanted device after receipt with other selected bits of the binary word or with bits stored within the implanted device. However, all of the verification and comparison takes place within the implanted device.

The U.S. Pat. No. 4,142,533 to Brownlee et al., entitled "Monitoring System for Cardiac Pacers" discloses a system for telemetering and monitoring the functioning of an implanted pacemaker as well as controlling the testing of the functions from a remotely located facility. The implanted pacemaker contains a telemetry system comprising transmitting circuitry, including an FM monitoring oscillator, and associated control circuitry which is actuated to initiate selected tests. The transmitting functions as well as the monitoring functions are powered by the power supply of the implanted device. Historical operating data is not provided.

The U.S. Pat. No. 4,237,895 to Johnson, entitled "Control Signal Transmitter and Monitor for Implanted Pacer", discloses a system for encoding and transmitting commands to effect modifications in the operating characteristics of an implanted pacer. Means for detecting and displaying monitored pacer operation is also disclosed. An oscillator outputs a carrier signal which is modulated to exhibit a fixed number of signal pulses with the width of the pulses modulated to exhibit a first (longer) duration and a second (shorter) duration. A receiver in the external device detects signals outputted by the implanted device representing pacer operating characteristics. The implanted pacer has receiving means, detection means and data processing circuitry for receiving, assimilating and storing coded signals and a transmitting system responsive to received signals. The pacer transmits a modulated signal representing the operation of the pacer. A flip-flop and counter system detects the interval between the transmitted pulses.

The U.S. Pat. No. 4,026,305 to Brownlee et al., entitled "Low Current Telemetry System for Cardiac Pacers," discloses a system for telemetering the performance of an implanted cardiac pacer incorporating a low power, low voltage, frequency-voltage sensitive pulse generator which supplies a pulse-interval-modulated telemetry output. The telemetry system embodies a telemetry pulse generator which is sensitive to input voltage. The nominal carrier center frequency of the pulse generator is pulse-interval modulated by the voltage of the power cell of the implanted device. Further modulation of the carrier indicative of other parameters is accomplished by other voltage inputs.

The U.S. Pat. No. 4,232,679 to Schulman, entitled "Programmable Human Tissue Stimulator" discloses an externally programmable implanted tissue stimulator with provision within the implanted device for verifying and screening control parameter words which are transmitted from an external controller. Readout of the stimulating signals and the tissue response thereto is provided for. The implanted device includes a plurality of memories in which are stored different parameters including all parameters necessary to control the characteristics of the stimulating pulses provided by the implanted device. The implanted device includes receiving and decoding circuitry designed to receive digital signals in the form of multibit parameter words of unique formats and decode them. Special decoding criteria in the implanted device are employed to ensure that only parameter words not affected by noise are permitted to vary the contents of any parameter in the implanted device. Verification is accomplished by transmitting the contents of any one of the memories out of the implanted device to the external device.

The U.S. Pat. No. 4,223,679 to Schulman et al., entitled "Telemetry Means for Tissue Stimulator System," discloses a telemetry system for use in a living tissue stimulator system in which an externally located oscillator is controlled by impedance changes in an impedance reflecting circuit located in an implantable tissue stimulator. The impedance reflecting circuit is either an LC or LR circuit providing either frequency modulation or amplitude modulation of the signal generated by the external oscillator. The externally located oscillator drives an LC circuit in which the inductor is positioned in a magnetically coupled relationship to an inductor in the implanted impedance reflecting circuit. A signal to be telemetered modulates an output frequency of a voltage controlled oscillator located in the implanted device. This frequency modulated output of the voltage controlled oscillator drives an FET switch which alters the impedance of the impedance reflecting circuit thereby modulating the output of the externally located oscillator.

A series of prior art patents commonly owned by Medtronic, Inc. of Minneapolis, MN disclose a communications link to an implanted cardiac pacemaker. The communications method comprises a programming head with a permanent magnet therein to cause a magnetically actuated reed switch within the implanted device to close. The closure of the reed switch in the implanted device enables the implanted device to accept signals from the external device which consist of rf pulse bursts which are separated by either a long or short time period representing one or the other binary digit. The implanted device performs various functions upon the detected signal including a parity check, an access code check and determining if the proper number of signals were transmitted within a given time. The implanted device can then signal the acceptance of a programming signal or reset the program acceptance circuit if extraneous signals are detected as programming signals. This series of patents are U.S. Pat. No. 4,236,522 "Asynchronous/Demand Mode Programmable Digital Cardiac Pacemaker," No. 4,236,524 "Program Testing Apparatus", No. 4,241,736 "Reset Means for Programmable Digital Cardiac Pacemaker", No. 4,250,884 "Apparatus for and Method of Programming the Minimum Energy Threshold for Pacing Pulses to be Applied to a Patient's Heart", No. 4,250,883 "Digital Cardiac Pacemaker with Refractory, Reversion and Sense Reset Means" and No. 4,257,423 "Medical Device."

It is therefore a first object of the present invention to provide a two-way coherent inductive communications link between a biologically implanted programmable medical device and an external device.

It is a second object of the present invention to provide a two-way coherent inductive communications link between a biologically implanted programmable medical device and an external device that is reliable and accurate.

It is a third object of the present invention to provide a two-way coherent inductive communications link between a biologically implanted programmable medical device and an external device that is reliable and accurate with reprogramming data immediately verifiable.

It is a fourth object of the present invention to provide a two-way coherent inductive communications link between a biologically implanted programmable medical device and an external device wherein command and programming data can be transmitted to the biologically implanted programmable medical device.

It is a fifth object of the present invention to provide a two-way coherent inductive communications link between a biologically implanted programmable medical device and an external device wherein status and stored data can be transmitted to the external device.

It is a sixth object of the present invention to provide a two-way coherent inductive communications link between a biologically implanted programmable medical device and an external device wherein the transceiver in the implanted device is powered by the inductive field powered by the external device.

Other objects, advantages and novel features of the present invention will become apparent from the following detailed description of the invention when considered in conjunction with the accompanying drawings.

SUMMARY OF THE INVENTION

The above-listed objects of the present invention are accomplished by a two-way coherent inductive communications link between an external transceiver and an internal transceiver located in a biologically implanted programmable medical device. Digitally formatted command data and programming data are transmitted to the implanted medical device by frequency shift keying the inductive communications link. The internal transceiver is powered by the inductive field established between the internal and external transceivers. Digitally formatted status and stored data are transmitted to the external transceiver by the internal transceiver amplitude modulating the inductive communications link using frequency shift keying. Immediate verification of the establishment of a reliable communications link is provided by determining the existence of frequency lock and bit phase lock between internal and external transceivers.

BRIEF DESCRIPTION OF THE DRAWINGS

The above-enumerated objects and novel features of the present invention will more fully appear from the following detailed description when read in conjunction with the accompanying drawings. It is to be understood that the drawings are for the purpose of illustration only and are not intended as a definition of the limits of the invention.

FIG. 1 illustrates a complete programmable implantable medication system (PIMS) of which the coherent inductive communications link of the present invention may form a part.

FIG. 2 is a simplified block diagram of the inductive coupled data link.

FIG. 6 illustrates the relationship of FIGS. 6A and 6B.

FIG. 6A is a schematic diagram of the MPU control logic and synchronous detector.

FIG. 6B is a schematic diagram of the MPU receiver and coil driver.

FIG. 7 illustrates the relationship of FIGS. 7A-7E.

FIG. 7B is a schematic view of the mode control and command format generators.

FIG. 7C is a schematic view of the MPU logic with R/I key generator.

FIG. 7D is a schematic view of the MPU logic frequency lock circuit.

FIG. 10B is a breadboard schematic of the IPIP control logic, subcarrier generator and telemetry format generator.

FIG. 15 is a timing diagram of the run/idle command sequence from the MPU.

FIG. 16 is a timing diagram of the received run/idle signals at the IPIP.

FIG. 17 is a timing diagram illustrating typical data to the IPIP microprocessor.

FIG. 23 illustrates the relationship of FIGS. 23A-23C.

FIG. 23A is a schematic view of the PPU crystal controlled oscillators and associated circuitry.

FIG. 23B is a schematic view of the PPU digital logic.

DESCRIPTION OF THE PRFERRED EMBODIMENT

Figure 3:
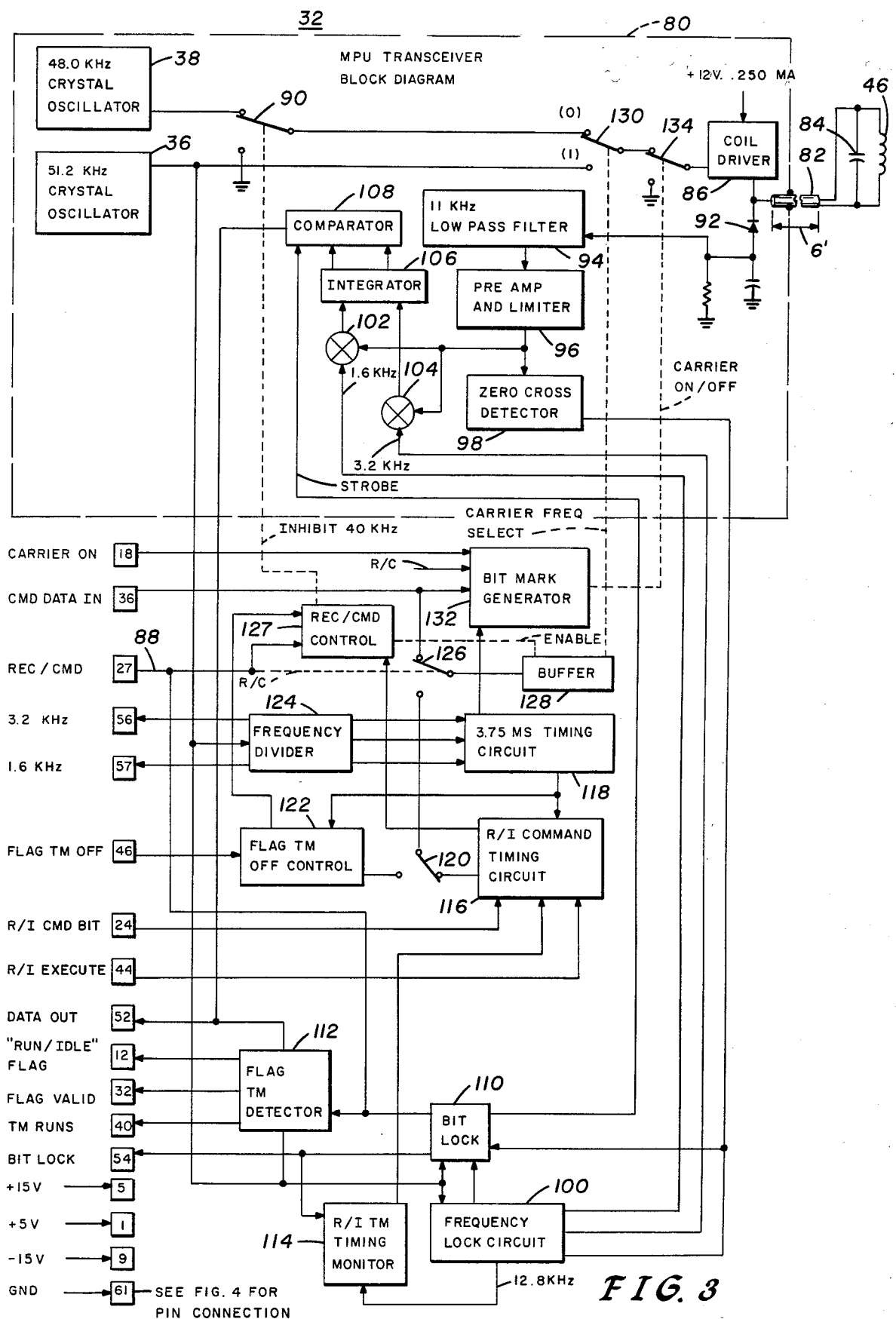
FIG. 3 is a block diagram of the MPU transceiver.

Referring now to the drawings, a description of the preferred embodiment will now be presented. To assist in the understanding of the present invention a discussion of the overall concept embodied in the complete system will first be presented. Referring to FIG. 1, the programmable implantable medication system (PIMS) 10 comprises generally two associated systems, a patient's system 12 and a remote control system called the medication programming system (MPS) 14. The patient's system comprises an implantable programmable infusion pump (IPIP) 16, a modem 18 with an associated communications head 20 and a patient's programming unit (PPU) 22. The modem 18 with associated communications head 20 allows communication with IPIP 16 from a remote location. The PPU 22 allows the patient to communicate with IPIP 16 at any time or any place as PPU 22 is a portable unit. The medication programming system 14 comprises a medication programming unit (MPU) 24 with an attached communications head 26 for direct communication with IPIP 16, a modem 28 for remote communications with modem 18 and a paper printer 30. The PIMS 10 provides an implantable reservoir and pump with microprocessor control of pump timing and a digital record of past operations.

The digital communications system, the subject of the present invention, provides communications capability between the IPIP 16 and external units 22, 20 or 26 at 200 bits per second. Communication capability is provided in three ways. A complete data readout and prescription change capability is provided by MPU 24 and communications head 26 at a medical facility. This requires the patient to be present. A remote communications capability is provided by modems 18, 28 and communications head 20 for patients who need monitoring and prescription or parameter modification while at their residence. These two communications capabilities utilize the electronics of MPU 24. The third communications capability is provided by PPU 22, a portable unit carried by the patient, which provides the patient with the ability to immediately adjust selected parameters in IPIP 16, for example, an insulin infusion rate adjustment at mealtime or during exercise. Basically, the system transceivers use the magnetic field from a 9 turn 3 inch diameter coil in the external transceiver to establish a communications link with the biologically implanted IPIP 16. The inductive link passes data at 200 bits per second in either (not both simultaneously) direction. Binary data to IPIP 16 sets various operational parameters such as time of pump operations and maximum allowable dose. It is noted that PPU 22 may be limited in allowable parameter changes to prevent a patient from either accidentally or purposely causing IPIP 16 to overdose. It is further noted that IPIP 16 may also have built-in limits to prevent accidental programming of an overdose by any external communications unit. Binary data from the implant provides confirmation of the control parameters and a history of recent operations of IPIP 16. Data transmission to IPIP 16 uses frequency shift keying (FSK) with a first frequency representing a binary "1" and a second frequency representing a binary "0". The frequencies of the preferred embodiment are 51.2 kHz for the first frequency and 48.0 kHz for the second frequency. A bit mark is provided at the start of each new bit value. The bit mark of the preferred embodiment is a 625 microsecond period of no transmitter output. Bit length is selected to be 5 mSec. Precision frequency and timing is provided by miniature quartz tuning fork resonators in COS-MOS linear oscillators, one at each transmitting frequency. Timing is derived from the 51.2 kHz oscillator. The return data path from IPIP 16 uses two subcarrier frequencies, a first frequency representing a binary "1" and a second frequency representing a binary "0". The subcarrier appears as a low level AM on the coil carrier waveform. It is generated by shorting out the IPIP 16 coil which changes the reflected impedance to the MPU 24 drive coil. This technique minimizes power and complexity requirements in IPIP 16. However, this imposes filtering and limiting requirements at the external driver since the subcarrier must be detected at levels of less than 1 mV peak to peak which is superimposed on the carrier which typically is 24 v peak to peak.

Another special feature utilized by the PIMS communications link is that IPIP 16 always starts communication in a "Run/Idle Telemetry Mode" when the external carrier is sensed by circuitry in IPIP 16. IPIP 16 alternately transmits its status "Run or Idle", then listens for a command from the external unit to go into normal communications mode. The Run/Idle Telemetry function provides verification that a proper communications link has been established prior to the external unit sending commands to IPIP 16 and provides a check of the IPIP 16 status. A further special feature is a "Run/Idle" command that switches IPIP 16 to the Idle mode for power reduction, for example, when the IPIP 16 is in storage prior to implant or if the patient's prescription is stopped for some period, and also to reset the IPIP 16 microprocessor if a software program error is suspected. This command is very secure for safety reasons and uses 32 bits in a special format. The idle command is sent at a faster rate than normal data. Additionally, the bit length is selected to be shorter than other data so it is transparent to the microprocessor. The bit length selected for this purpose is 3.75 mSec per bit. The "Run/Idle" command allows communications tests to be conducted without affecting normal programming since the command "Run" may be sent repeatedly. Each "Run" or "Idle" Command accepted by IPIP 16 switches the IPIP transceiver into the "Run/Idle Telemetry Mode."

Control and data signals for MPU 24 may be input from a desk top microcomputer under the control of a doctor, nurse or other medical person. The microcomputer formats the instructions in compatible binary words. The microcomputer presents data received from IPIP 16 on a CRT in graphical or alphanumeric form. The system also comprises paper printer 30 which provides a permanent record of programming instructions and past operations from data transmitted by IPIP 16.

Referring now to FIG. 2, there is presented a simplified block diagram of the inductively coupled data link comprising an external transceiver 32 and the IPIP transceiver 34. The external transceiver 32 comprises a first crystal oscillator 36 and a second crystal oscillator 38 both with outputs to a switching means 40 controlled by digital control electronics 42. First crystal oscillator 36 also has an output to digital control electronics 42. It is noted that although the preferred embodiment calls for crystal oscillators any source of precise frequency generation could be substituted therefor. Digital control electronics 42 controls the operation of switching means 40. The output of switching means 40 is input into power driver 44 which drives coil 46. Receiver 48 is connected to a lead of coil 46. Power driver 44 also has an input from digital control electronics 42. Receiver 48 outputs the 200 bits per second data, which is transmitted from IPIP transceiver 34 to another portion (not shown) of MPU 24 (FIG. 1). The 200 bits per second data is also input to digital control electronics 42. Receiver 48 also has an input and an output to digital control electronics 42. Digital control electronics 42 has an output to power driver 44 and output flags 50 to other portions (not shown) of MPU 24 (FIG. 1). Digital control electronics 42 is input with control lines 52 and is input with 200 bits per second data from another portion (not shown) of MPU 24 (FIG. 1) which is to be transmitted to IPIP transceiver 34.

IPIP transceiver 34 is separated from external transceiver 32 by being implanted beneath the skin represented at 54. The complete IPIP 16 system is encased in a body fluid impervious container such as a 3AL-2.5Va Titanium case 56. The IPIP transceiver 34 comprises a coil 58 (note that coil 58 is within case 56) with one lead to ground and the other lead connected to one terminal of switching means 60, to digital discriminator 62 and to power conditioner and enable 64. Power conditioner and enable 64 has an input from a 3.6 V battery (not shown) and a clock request output 66 and an output 68 to timing and control 70 and digital discriminator 62. Timing and control 70 controls switching means 72 and switching means 60. Switching means 72 is switchable between three terminals comprising 1.6 kHz and 3.2 kHz outputs from timing and control 70 and a modulation off control terminal 74. Timing and control 70 and digital discriminator 62 each have a precise frequency input 76 from a precise frequency generator (not shown) in another portion of IPIP 16 (FIG. 1). Timing and control 70 has control lines 78 input thereto and a data input of 200 bits per second which is to be transmitted to external transceiver 32 from a microprocessor (not shown) located in another portion of IPIP 16 (FIG. 1). Digital discriminator 62 outputs 200 bits per second data to a microprocessor (not shown) received from external transceiver 32 and outputs 267 bits per second command data to a "Run/Idle" decoder (not shown) located in another portion of IPIP 16 (FIG. 1).

Referring now to FIG. 3 there is presented a more detailed block diagram of the external transceiver of MPU 24 (FIG. 1). A description of the external transceiver embodied in PPU 22 will be presented below. Note that circuitry for frequency generation, driving the communication coil and receiving is completely enclosed in an electrostatic shielded enclosure represented by dashed outline at 80. Enclosure 80 is penetrated only by filtered lines and coaxial cable 82 leading to coil 46. It is herein noted that the description of the preferred embodiment describes specific components, however, it is emphasized that the specificity of the description is for illustrative purposes only. It is to be appreciated that substitution of other specific parts for these specified herein may be accomplished by one of ordinary skill in the art without detracting from the inventive concept embodied herein and that the scope of the invention is embodied in the appended claims. Coil 46 is a three inch diameter, 9 turn (#24 solid copper) communications coil and is connected to the electronics within shielded enclosure 80 by coaxial cable 82 which is a six foot length of RG-178. Mylar tuning capacitor, represented by 84, are mounted at coil 46. Coil 46 is encased in an electrostatic shield of copper sheet (not shown) to reduce the coil susceptability to interference. The current through coil 46, which is approximately 1.5 amperes at either 51.2 or 48.0 kHz, establishes a magnetic induction field of sufficient energy to power the titanium enclosed IPIP transceiver 34 (FIG. 2) out to a separation of about four inches. A PNP power transistor (FIG. 4 to be discussed below) within coil driver 86 pulses coil 46 during part of the positive voltage excursion. Coil Q of coil 46 is low enough to pass both the 51.2 and 48.0 kHz frequencies, however, the coil is tuned to 50.0 kHz to slightly favor the 51.2 kHz in order to insure maximum advantage during the receive mode (to be discussed below). The drive current through coil 46 is shaped by an RC time constant coupling the square wave to the PNP power transistor base and an inductor in the PNP emitter. The purpose of the shaping is to minimize distortion of the coil 46 waveform and to lower the power dissipation of the PNP power transistor. Details of the transceiver driver will be discussed in conjunction with FIG. 5.

During the period when external transceiver 32 is to receive data from the implanted IPIP transceiver 34 (FIG. 2) a "Rec/CMD" command 88 causes switching means 90 to mute the output of the 48.0 kHz crystal oscillator 38 by shorting the drive line to ground. This prevents oscillator crosstalk from generating a phantom 3.2 kHz (51.2−48.0 kHz=3.2 kHz) in the receiver output. The crystal oscillators 36, 38 are shielded from each other to further minimize the generation of oscillator crosstalk. As also can be appreciated, the drive signal and power supply at the PNP power transistor must be very clean to maintain receiver sensitivity at the four inch range (external transceiver coil 46 separated from implanted transceiver coil 58 (FIG. 2) by four inches). Data from IPIP transceiver 34 (FIG. 2) (to be discussed in detail below) is transmitted by shorting out the IPIP coil 58 (FIG. 2) for 50% of the desired subcarrier period, either 1.6 or 3.2 kHz. Shorted IPIP coil 58 (FIG. 2) reflects a changed impedance to external transceiver coil 46 which changes its tuning and loading, producing a small amount of subcarrier AM on the carrier waveform envelope. The subcarrier AM is detected by a simple diode AM detector 92 by demodulating the subcarrier envelope. The diode 92 conducts at the negative peak voltage (note from discussion above that the driver PNP power transistor is only on during part of the positive excursion). The detected subcarrier varies from a fraction of a millivolt peak to peak at extreme range to several hundred times that level. The output of AM detector 92 is input to a receiver section comprising an 11 kHz low pass filter 94 and then to a preamp and limiter 96 which provides filtering, amplification and limiting to provide a squared-up waveform for the following components. All amplifier stages are differential "long tail pairs" and have no saturation or storage problems. The output of preamp and limiter 96 is input to zero cross detector 98 which comprises a comparator which provides a squarewave with good risetime for digital circuitry. The output of zero cross detector 98 is a replica of the original subcarrier generated in IPIP 16 (FIG. 1), delayed in time by filtering and subject to some time jitter due to receiver and external noise. The output of zero cross detector 98 passes through shielded enclosure 80, via an RFI filter (not shown) to frequency lock circuit 100 where it is used to phase lock a coherent reference frequency divided down from 51.2 kHz generated by crystal oscillator 36. The coherent reference frequency utilized in the preferred embodiment is 1.6 kHz and in the preferred embodiment can only be varied 19.5 microSec (one 51.2 kHz period) per cycle so that up to 10 milliseconds will be required for initial lock. The slow adjustment gives the 1.6 kHz reference frequency and the 3.2 kHz frequency also used as a coherent reference frequency (which is obtained from the divider stage prior to obtaining the 1.6 kHz) "flywheel" characteristics so that short noise bursts cannot cause major timing errors and coherent detection can be used. The coherent 1.6 kHz and 3.2 kHz frequencies are output from frequency lock circuit 100 and each input into separate synchronous detectors 102, 104 where they are mixed with the output from preamp and limiter 96. The synchronous detectors 102, 104 drive an integrator 106 which is connected across the two inputs to comparator 108. The integration capacitor is reset following the strobe at 3.75 mSec after start of bit. It charges up from zero for 3.75 mSec of each bit at which time a "decision" is made by strobing the comparator output. The strobe and reset timing is provided by bit lock circuit 110 which time locks on the instant the subcarrier (either 1.6 kHz or 3.2 kHz) frequency changes. This synchronous detection provides good rejection of motor and switch spike noise, also the resulting broadband signal to noise ratio is significantly better than that available using the basic 5 kHz wide input filter circuit. Bit lock circuit 110 also provides a "Bit Lock" flag which signifies that the external transceiver 32 has achieved both frequency lock and bit lock and thus that the data has a high probability of being correct. The "Bit Lock" flag is also used to cause an LED on the communications head 20 or 26 (FIG. 1) to glow providing immediate confirmation of an established communications link. Flag telemetry detector 112 determines the mode (Run or Idle) of the IPIP when the communications link is initiated and after any Run/Idle command by verifying that bit lock occurs with a constant subcarrier frequency for greater than 80 mSec. This situation corresponds to a Flag (Run/Idle) TM readout only when the IPIP is in Flag TM mode (to be discussed in detail below). Flag TM mode occurs automatically when a communications link is established (by moving an energized coil close enough to the implanted coil or when the carrier is turned ON if the coil is already in place or when a Run/Idle command is accepted by IPIP). Flag TM is turned OFF by the transceiver as instructed by the external control computer after which neither Run/Idle Flag nor the Flag Valid bit (which confirms the 80 mSec of constant signal) is meaningful. The MPU transceiver 32 always initiates communications in its receive mode which allows it to verify the establishment of a reliable communications link from the Bit Lock and Flag Valid flags when the IPIP transceiver comes on in Run/Idle telemetry mode. The 48 kHz oscillator 38 is muted and coil drive selector 130 is continuously connected to its 51.2 kHz drive. Once the link is confirmed the user has two options; one, to stop the R/I telemetry or 2, to send a R/I command and change the IPIP status. Stopping the R/I telemetry puts the implanted IPIP transceiver under control of the implant microprocessor and allows data transfer from IPIP and transmission of instructions to its RAM.

The MPU transceiver 32 goes to transmit mode under three conditions. The transmit mode requires the 48 kHz oscillator output enabled and data buffer 128 control of modulation switch 130. The Rec/Cmd control 127 enables the data buffer 128 and the 48 kHz oscillator 38 if any one of the following conditions is true:

1. input Rec/Cmd pin 27 is LO;
2. input Rec/Cmd pin 27 is HI and a Run/Idle command is initiated; or
3. input Rec/Cmd pin 27 is HI and a Stop TM command is initiated.

The R/I command and the Stop TM command are each 480 mSec in duration after which time the input Rec/Cmd pin 27 again controls the transceiver mode. R/I command timing circuit 116 provides special timing which is required to synchronize the Run/Idle command when the IPIP is in the Run/Idle telemetry mode. The command must initiate immediately after the IPIP switches from transmit to receive as monitored by the R/I TM Timing Monitor 114. Run or Idle for the command is previously selected by the level at input pin 24 after which R/I Execute pin 44 going HI starts the logic looking for a Bit Lock HI to LO transition. These occur every 320 milliseconds when IPIP is sending R/I telemetry. If Bit Lock remains LO for 640 milliseconds the IPIP is not in telemetry mode and the command is transmitted assuming IPIP is in normal receive condition. A Run/Idle command sequence consists of 128 bits at 3.75 millisecond per bit with every bit time starting with a 625 microsecond Bit Mark. One additional Bit Mark is added at the end of the command when the output returns to continuous 51.2 kHz so that the entire sequence is transparent to the implanted IPIP microprocessor. The completion of a successful command is acknowledged by the IPIP going into or back into the R/I telemetry mode and verifying the command mode, Run or Idle. Command through IPIP telemetry is possible when initiated at the beginning of the 160 millisecond read portion of the TM cycle because the IPIP command decoder clamps the IPIP transceiver in receive after it receives the first 16 bits of a proper command sequence (about 60 milliseconds after initiation of the command). Thus, the entire 480 millisecond command will be accepted as long as the first 60 milliseconds occur during the 160 millisecond TM read interval. The TM Off command is a 480 millisecond interval during which the carrier frequency is set to 48.0 kHz and bit marks are generated every 3.75 milliseconds. Again, one extra bit mark is inserted after switching the carrier back to 51.2 kHz at the end of the command to keep the operation transparent to the IPIP microprocessor. This technique works because the IPIP microprocessor channel discriminator requires 3.906 milliseconds to detect a new bit and the Bit Marks keep resetting it every 3.75 milliseconds. The IPIP command channel discriminator counts for 2.578 milliseconds only. The Bit Marks are generated by switching 134 to ground for 625 microseconds at the beginning of each 3.75 millisecond bit period. No time synchronization is necessary to insure TM stop, the 480 millisecond duration will blanket at least one 160 millisecond receive interval at the IPIP, stopping TM. TM Stop may be initiated with the Rec/Cmd control pin 27 in either the HI or LO state.

Normal data communications with the IPIP microprocessor is achieved after verifying the communications link integrity (monitoring the Bit Mark), IPIP status (Run or Idle) from the TM data, and stopping TM. All control for the MPU transceiver is then from its local computer terminal. Data is transmitted to the IPIP whenever Rec/Cmd control pin 27 is LO and the CMD Data In pin 36 is driven. The FSK output is directly controlled by the input data which switches 130. A Bit Mark is generated internally in the transceiver only when the input data changes, i.e., 1 to 0 or 0 to 1. This minimizes the IPIP transceiver power consumption and improves the noise rejection. Bit length timing of 5.00 milliseconds is provided by the data input signal.

Normal receive mode in the MPU transceiver occurs when Rec/Cmd control pin 27 goes HI. However, the synchronous detection system requires a preamble sequence from the IPIP modulation to insure frequency and bit lock prior to processing data. Each IPIP data readout starts with 10 milliseconds of continuous 1.6 kHz subcarrier followed by the digital word FF. The preamble is needed only at the start of receive from IPIP after which coherent lock will be maintained indefinitely as long as a subcarrier is present. Normal data communications can be maintained as desired. Data Communication utilizes "Handshakes" between the implant and external device to achieve 100% verification of any new prescription schedule or mode change after which an "execute" message is sent. Each time the MPU mode is changed to receive the IPIP, the message will start with a preamble. No special technique is needed when sending data to the IPIP other than maintaining the proper bit timing and inserting Bit Marks when data value changes. The IPIP will not go back into TM readout unless a Run/Idle command is sent or the inductive link is broken for an extended interval (more than a second, typically, depending on the range to the implanted device).

Communications are terminated by removing the external coil from the vicinity of the implant or by turning OFF the carrier. The IPIP transceiver will go back to IDLE mode as soon as its power conditioning filter capacitors discharge (to be discussed below). A resumption of the carrier, by placing the external device near the implant, will initiate a new sequence of events starting with IPIP Run/Idle telemetry.

Figure 4:
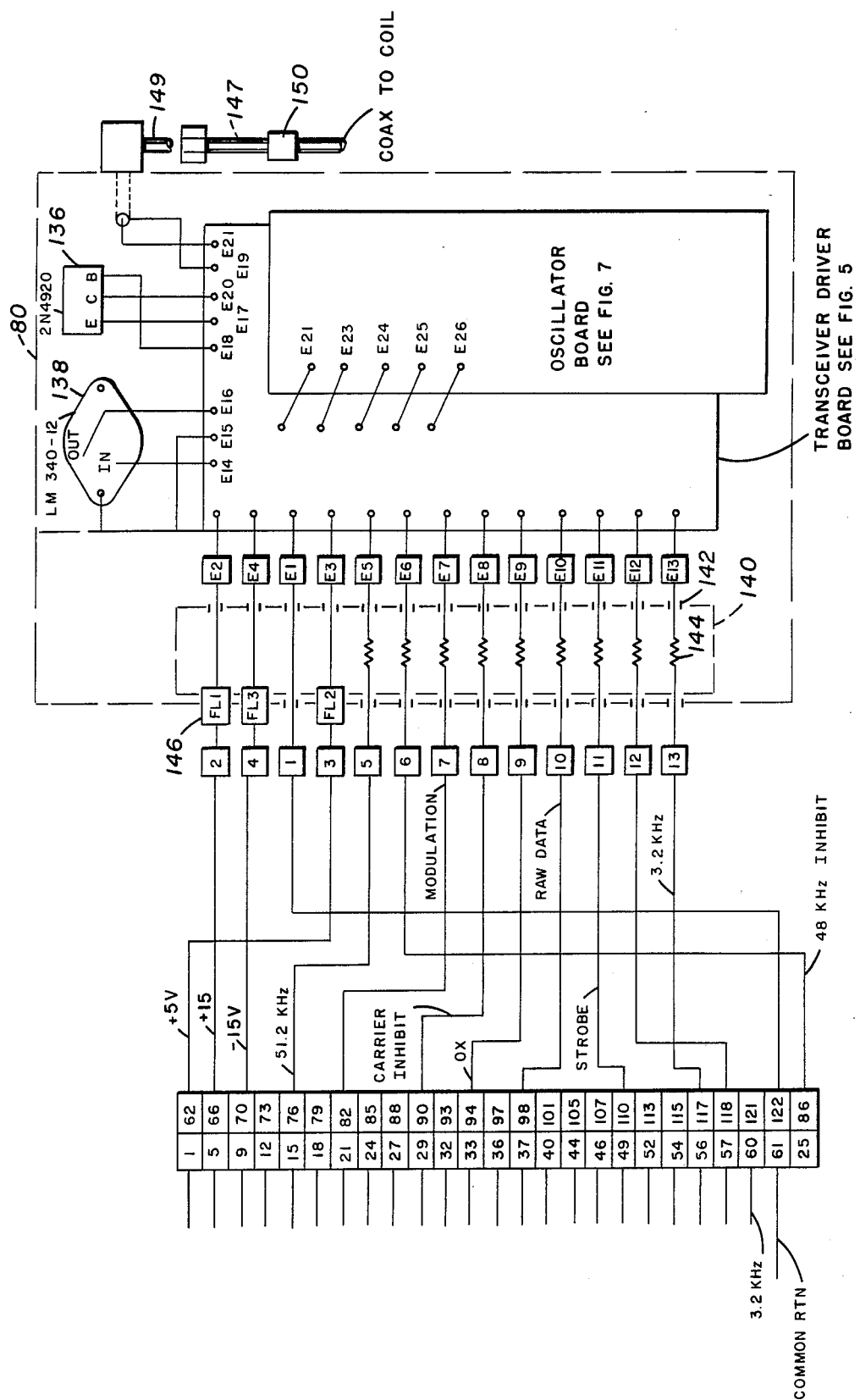
FIG. 4 is an illustration of the interface between the external transceiver and the digital portions of the external device.

Referring now to FIG. 4, the interface between the transceiver and digital portions of the preferred embodiment are detailed. It is again emphasized that the detailed discussion is for illustrative purposes only and that modifications can be made by one of ordinary skill in the art without denigrating from the basic inventive concept embodied herein. The shielded enclosure 80 (7259–4300) is an electrostatic shield and connects only to the coax shield from the communications coil and the incoming ground reference (Pin 61). It is electrically insulated from the outer shields and main enclosure to prevent current loop crosstalk in the coil driver, coil, AM detector and receiver circuits (FIG. 3). Oscillator circuits are also individually shielded within shielded enclosure 80 to further eliminate crosstalk between the oscillator circuits 36, 38 (FIG. 3). The coil drive transistor 136 which may be a 2N4920 and series voltage regulator 138 which may be an LM 340-12 are bolted to shielded enclosure 80 for thermal sinking and are a part of the shield 80. The 2N4920 requires a kapton insulator and isolated mounting hardware. The voltage regulator, LM 340-12, case is at shield ground, therefore no special hardware is needed. Interconnections from circuitry within shielded enclosure 80 and circuitry external thereto are routed through isolation filters in a shielded compartment 140. Isolation for the digital signal lines is provided by 1000 pf feedthrough capacitors 142 and series 510 ohm resistors 144. Power leads are routed through compartment 140 through LC isolation filters 146 having low DC resistance. Ground is direct through feedthrough capacitors. The digital board 148 is a standard Augat wire-wrap board with 122 pins. The PNP coil driver 136 output and AM detector 92 (FIG. 3) input connects to a coax cable 147 by an Omni Spectra OSM 601-5 plug 149. Cable 147 connects to connector 150 which has a floating (shield not grounded) coax feedthrough and four pins for other circuitry such as the bit lock indicator LED. Connector 150 outputs to the communication head, 26 FIG. 1., which is a 3" diameter potted assembly which includes 9 turn coil 46 (FIG. 3), a coil electrostatic shield and the bit lock LED.

Figure 5:
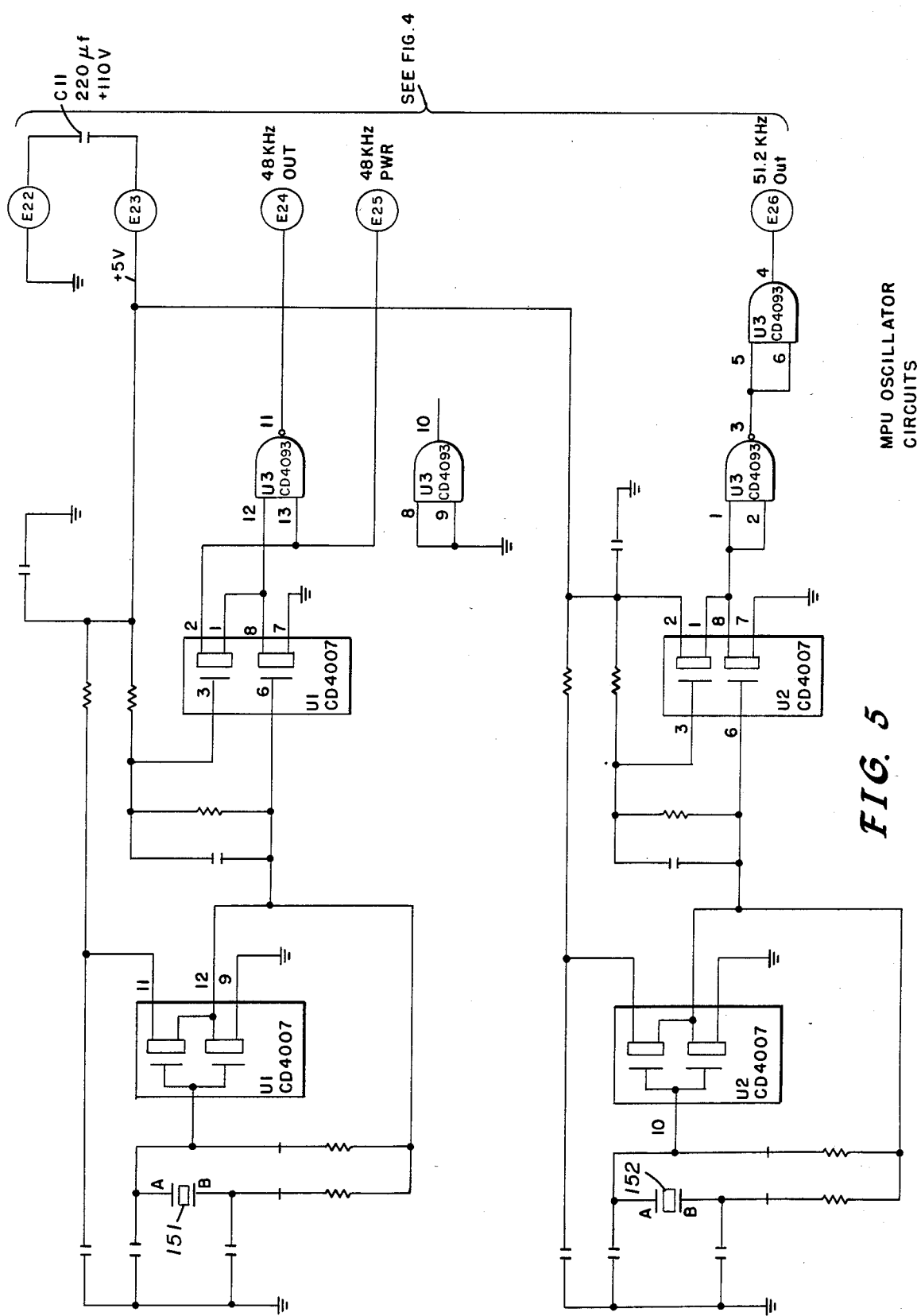
FIG. 5 is a schematic of the MPU oscillator circuits.

Referring now to FIG. 5, the oscillator circuit of the preferred embodiment will now be described. The two quartz resonators 151, 152 are miniature tuning forks tuned to 48.0 kHz and 51.2 kHz respectively. Their electrical characteristics are similar to the conventional quartz crystal. Both oscillators run continuously once power is applied to the transceiver. The output of the 48.0 kHz oscillator is muted, as discussed above, during the period that the external transceiver is in the receive mode to prevent crosstalk. Muting is achieved without stopping the oscillator by removing power from U1-2 and grounding it. The layout, grounding, shielding and power filtering is critical in maintaining a clean 51.2 kHz output during the receive mode.

Referring now to FIG. 6, a description of the transceiver driver of the preferred embodiment will now be presented. U1 shown at 154 is a CD 40109 level translator to translate the reference oscillator signals, modulation signal and carrier inhibit lines from a 5 V logic level to the 12 V coil driver bus. The CD 40109 has the following 12 V logic outputs:
Pin 4—51.2 kHz;
Pin 11—Data for Modulation;
Pin 5—48.0 kHz (Grounded during receive); and
Pin 13—Carrier Inhibit.

The data line at U1-11 selects either the 51.2 or 48.0 kHz for coil drive by enabling either U2-3 or U2-4. The chosen frequency drives U2-12 whose output is gated by the control line, "Carrier Inhibit." The output at U2-11 drives five parallel sections of U3, shown at 155. The outputs of U3 are AC coupled to the base of the 2N4920 PNP coil driver 136 (FIG. 4) via connector E-18. The conduction time of the coil driver is determined by the specific power transistor selected and the C5-R1 time constant, shown at 156, 157 respectively. The inductor L1, shown at 158, is inserted in series with the PNP emitter, via connector E-17, to minimize distortion and power dissipation in the power transistor. The transistor is biased to conduct for about half the positive voltage swing of coil voltage. The operating point is trimmed so that the current drain varies no more than about 50 mA from the nominal 150 mA. This adjustment is not critical and the current will normally vary between the two carrier frequencies. The nine turn three inch diameter communications coil 46 in the external transceiver has an inductance of about 12.4 microhenries and a Q of approximately 10. It is connected by 6 feet of RG178 coax and is driven for only part of its positive voltage swing and is easily modulated by remote inductive coupled loads. The modulation caused by remote reactance changes is greatest when there is no drive current through coil 46 (FIG. 3), i.e., during the negative swings. Amplitude modulation on the 51.2 kHz carrier (the 48.0 kHz carrier is muted during the receive mode) is detected by diode 160 at the peak negative voltage. The following LC lowpass filter circuit, shown at 94 reduces the carrier component prior to driving the three stage amplifier 96. Three stage amplifier 96 is designed to provide hard limiting over the entire communication range. Signal degradation at extreme range is observed as jitter in the zero cross times and slow risetimes. The limiting provided by amplifier 96 gives immunity from both external electrical noise and low frequency mechanical AM caused by coil movement (both external coil and implanted coil) caused by patient movement such as breathing, etc. The components of amplifier 96 have well matched transistors and a balance pot 162 which trims out residual offset DC. Balancing is accomplished by placing an IPIP at maximum range and adjusting balance pot 162 for best symmetry of the subcarrier as observed at either point 164 or 166. Low frequency rolloff is achieved by coupling capacitor 167 and the network driving points 168, 169. Since both points 168, 169 have identical DC drive voltages, there is no DC differential output from the stage. Point 168 has a 110 microsecond high frequency rolloff and point 169 has a 25 microsecond rolloff. Frequencies lower than 1 kHz are attenuated by the differential characteristics of the long tail pair and frequencies above 6 kHz are attenuated directly by the input networks. Capacitor 170 provides additional high frequency rejection to minimize stray coupling from driver PNP 136 (FIG. 4). Noise level referred to the input at pin A of diode 160 is approximately 70 microvolts rms. The differential noise output at points 164, 166 is approximately 140 microvolts rms. Gain from inductor 171 pin A to pin 11 of U4, indicated at 172, is approximately 30 at 1.6 kHz and approximately 20 at 3.2 kHz. The passband differential gain from diode 160 pin A to U4 at 172, 173, is approximately 14. The U4 differential pair, at 174, 175 has a differential gain of about 35 depending on the actual current of the CR6 bias source, indicated at 176 which is between 1.8 and 2.2 mA. The differential input between 174 and 175 must be in excess of 400 millivolts peak to peak to obtain a squarewave limited output from the following transistor pair $Q_1$ and $Q_2$. Overall gain from pin A of diode 160 to points 164 and 166 is approximately 3000. Operating point for the receiver is critical and is adjusted by pot 162 for best output signal symmetry at extreme range. As can be appreciated, the DC levels depend on the current source diodes and thus vary about 10% from unit to unit. The entire receiver is DC coupled with the input bases set by diode 177 at approximately −6.8 Volts. The resistors specified for the receiver section are 1% metal film so that temperature coefficient and long term drift will be small with respect to variations caused by current source tolerances. The preferred embodiment specifies the metal film resistors since a shift in differential loading would degrade operations. U6, shown generally at 178, is a dual comparater package. Pin 1 output of the dual comparater 178, indicated at 179, is the zero crossing (OX) detector which provides a continuous signal to the transceiver digital section (FIG. 7 to be discussed below). It has approximately 10 mV of DC hysteresis and 100 mV of transient positive feedback with a time constant of 23 microseconds to minimize noise sensitivity. The coherent detection system employed in the present invention rejects pulse noise within one bit time. Pin 7 output of the dual comparator 178, indicated at 180, senses the filtered output across capacitor 181 from the coherent detectors, 182, 183. The timing for coherent detection as utilized in the present invention is shown in FIG. 8. Coherent frequencies at 1.6 and 3.2 kHz are phase locked to the subcarrier (OX) at the beginning of each data readout from the IPIP (IPIP Data). The differential input to U6 pins 5 and 6 [(U6-5) to (U6-6)] is the integrated differential output from the coherent switching which builds up during the first 3.7 mSec of each 5.0 mSec bit time. A bit lock circuit 110 (FIG. 3) in the digital electronics section (to be discussed in detail in conjunction with FIG. 7) is phase locked to the 5 mSec bit interval. It produces a signal (DATA STROBE) which goes HI for the last 1.25 mSec of each bit time. The leading edge strobes the state of U6-7, at 180, FIG. 6, into U7-1, FIG. 6. The DATA STROBE pulse is delayed about 10 microseconds by the R-23, C-13 network, indicated generally at 182, FIG. 6, after which switch U5A, at 182.5, discharges capacitor 181 to preset a zero differential input to the comparator 178 at the beginning of the next bit time. Switch U5A, at 182.5 opens at the start of the next bit, about 10 microseconds after DATA STROBE goes LO. Coherent detector 184 switches 182 and 183 at 1.6 kHz and 3.2 kHz respectively. The cos-mos switches act as synchronous rectifiers for the subcarrier producing the differential voltage shown in FIG. 8 as "(U6-5) to (U6-6) FIG. 6 Differential Input." The flywheel characteristic of the coherent reference drive frequencies maintains proper-coherent phase against pulse noise input tending to average such error to zero. It is emphasized that reception at extreme range requires minimal noise from the PNP power transistor 136 (FIG. 4), carefully routed ground returns and a well muted and shielded 48.0 kHz oscillator 38, FIG. 3. This describes the external transceiver receiver section utilized in communications leads 20 or 26 (FIG. 1).

A much simplified receiver is used for the patient controlled PPU 22, FIG. 1, which operates using short data exchanges. Output is derived in the PPU 22 from the total number of zero crossings during the previous 5 mSec period and requires no timing or frequency lock to the zero cross subcarrier outputs. Communication with either the above described MPU receiver or the PPU receiver requires data handshakes for initial access. The short data exchanges of the PPU may be repeated if not confirmed. In addition, the PPU 22 requires no limiting amplifier, the AM detector filter output drives a sensitive comparator directly. The PPU 22 will be discussed in more detail below in conjunction with FIGS. 22–23.

Figure 9:
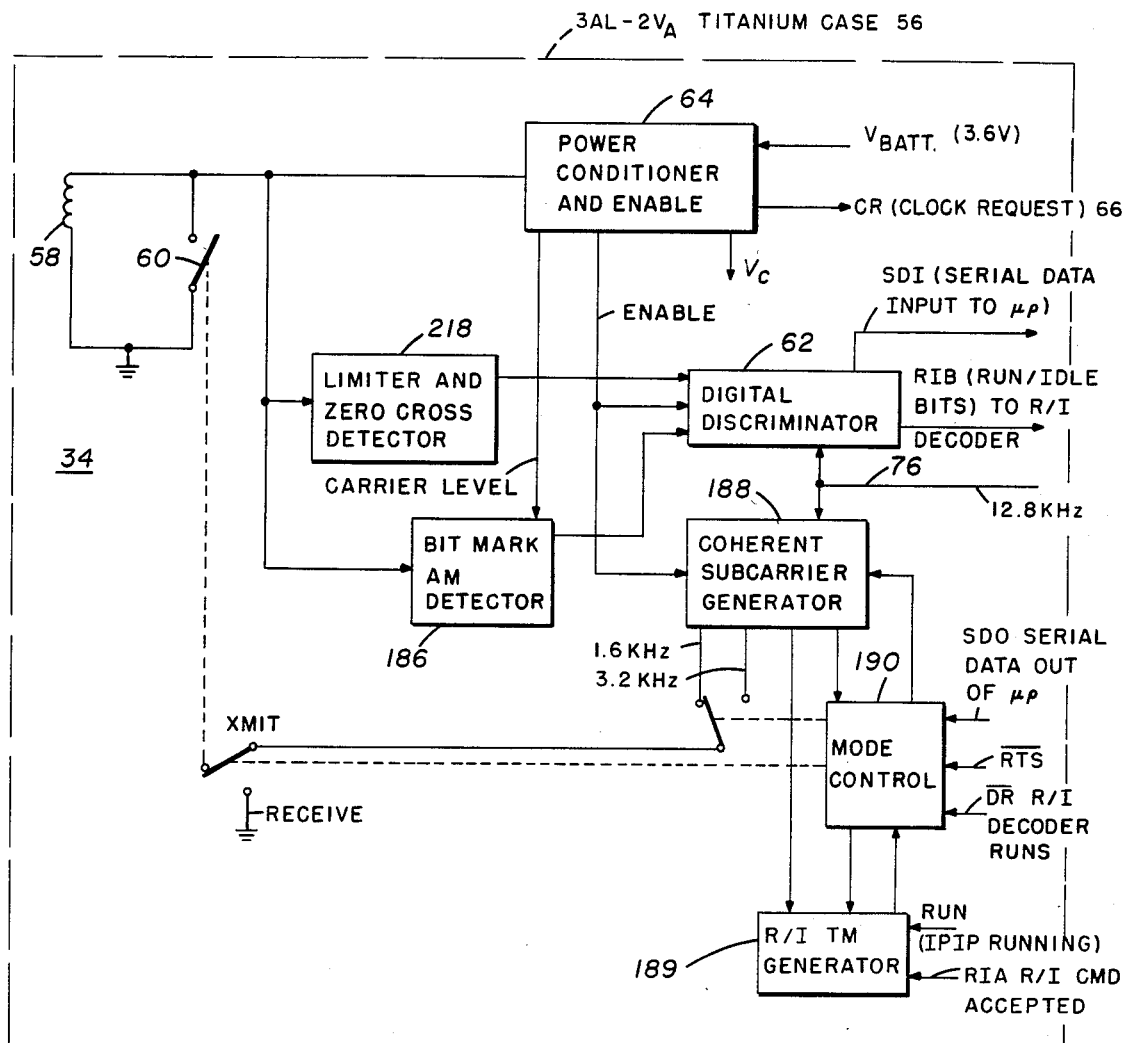
FIG. 9 is a block diagram of the IPIP Transceiver.

Referring now to FIG. 9, a more detailed block diagram of the IPIP transceiver 34 is presented. Generally, the implanted IPIP transceiver 34 is a digital 200 bits per second communication transceiver that features low standby current (1.5 microamps) and is powered by the inductive external field generated by the coil during communications. There are two receiver outputs to other parts of the IPIP, one to the microprocessor and a second to a special "Run/Idle" command decoder. Transmission to and from the IPIP transceiver is coherent and requires minimum power from the IPIP battery. The communications link to the IPIP utilizes carrier frequency shift keying at 48.0 and 51.2 kHz and the return communications link from the IPIP utilizes frequency shift keying between AM subcarriers at 1.6 and 3.2 kHz. The transceiver, including the transmission coil, is completely enclosed in a titanium case, shown at 56 and communications are effected at ranges in excess of two inches. The power conditioner and enable 64 contains a capacitive voltage doubler. The inductive link drives the doubler which stores its output on a 1 microfarad capacitor. (A more detailed description will be presented below in conjunction with FIG. 10). The doubler is followed by a voltage regulator that also contains the "Enable" sense function. IPIP transceiver 34 will be powered and enabled whenever the regulated voltage is equal to the battery voltage. A 56 kohm resistor is added to the regulator load during the initiation period and removed when "Enable" occurs. This insures the link is producing sufficient energy to power the transceiver. Maximum drain from the link is about 80 microamps at the time of "Enable." The "Enable" condition also sends a "Clock Request" (CR) shown at 66 to the IPIP precision reference 12.8 kHz circuit (not shown) which turns on the 12.8 kHz input to the transceiver. If the IPIP is in the "IDLE" condition with the clocks turned "OFF," the CR line 66 will power up the precision clock (which takes about a second to come on line) after which communication can be effected. Data is transmitted to the IPIP by shifting the link carrier between 48.0 kHz which represents a binary "0" and 51.2 kHz which represents a binary "1". The frequency shift keying has a very favorable signal to noise level since the link output must be several volts before the transceiver is powered. A simple resistor diode limiter removes any AM from the input. Digital discriminators 62 are utilized to minimize volume since no passive elements are needed, to eliminate the need for tailoring and to allow operation without restricting the rates of the internal precision clock to the incoming FSK frequencies. The digital discriminators are simple counters with gate duration set by the precision clock and a counter. Bit time is synchronized by a "BIT MARK" at the initiation of each bit. The "Bit Mark" is 100% AM, i.e., carrier turned OFF for about 625 microseconds. The "BIT MARK" signifies the beginning of a bit interval that may be 5.00 mSec (data to microprocessor) or 3.75 mSec (data to Run/Idle command detector). The use of two different intervals allows the Run/Idle command sequence to be transparent to the microprocessor. This will be explained in specific detail below in conjunction with FIG. 10. The "BIT MARK" is the most noise sensitive time during communication. Noise rejection is enhanced by storing the voltage doubler level for carrier ON operation and requiring the bit mark detector 186 drive to exceed about 0.6 the FSK peak amplitude prior to initiating the discriminator counters. Communication timing is illustrated in FIG. 11. The 3.75 mSec Run/Idle bit interval is short enough so that the microprocessor discriminator never reaches its 3.906 mSec count interval and SDI remains unchanged during RIB communication. Communication from the IPIP transceiver to the external unit uses 1.6 and 3.2 kHz subcarriers impressed on the transmitted signal as very low level AM. Switch 60 across coil 58 illustrates the modulation technique. A low impedance load, such as a VFET, shorts out coil 58 changing its reflected loading. As discussed above, this results in AM modulation of the carrier at the external generator which is detected by a conventional diode detector, amplified, filtered and limited to produce clean FSK at 1.6 and 3.2 kHz. The IPIP switch 60 is a VFET with very high input impedance and no power is required from either the battery or regulator circuit for modulation. A 1 microfarad capacitor in the power conditioner and enable 64 carries the transceiver load (less than 20 microamps during transmit) during the modulation periods. The modulation is coherent in that the two subcarrier frequencies are obtained from a ripple counter in coherent subcarrier generator 188 and bit switching always occurs on a negative transition. This allows coherent detection in the external unit.

Figure 12:
FIG. 12 is a timing diagram of the run/idle format.

Data from the microprocessor is on the Serial Data Output (SDO) line and time synchronized in the transceiver. Run/Idle telemetry, generated by R/I TM Generator 189, is a special format used to transmit one bit of information (Run or Idle) and occurs immediately after initiating the link to allow verification (the subcarriers are detected in the external transceiver) and status check. The Run/Idle Telemetry Format is shown in FIG. 12. The IPIP transceiver alternately transmits and listens every 160 mSec during R/I TM. Continuous 48.0 kHz during the listen interval shuts R/I TM OFF after which the $\overline{RTS}$ signal (Ready to Send NOT) controls the mode 190. The IPIP transceiver has four basic modes of operation-*Standby, R/I TM, Receive* and *Transmit.* Unless in Standby or R/I TM, the mode is controlled by the line $\overline{RTS}$ (Ready to Send NOT). The transceiver goes to the R/I TM mode at every initial link "Enable" time and also whenever a successful R/I command has been achieved. R/I telemetry can be interrupted by a R/I command. This is necessary to allow RESET of the microprocessor in the event of $\overline{RTS}$ held LO. If the external transceiver initiates an R/I command at the beginning of the R/I TM "listen" interval the $\overline{DR}$ (Decoder Runs NOT) line goes LO maintaining receive mode until the command is accepted or aborted. The limiter and zero cross detection 218 has an input from coil 58 and an output to digital discriminator 62.

Figure 10:
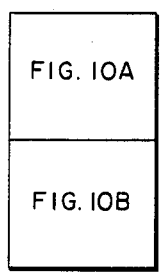
FIG. 10 illustrates the relationship of FIGS. 10A and 10B.
Figure 10A:
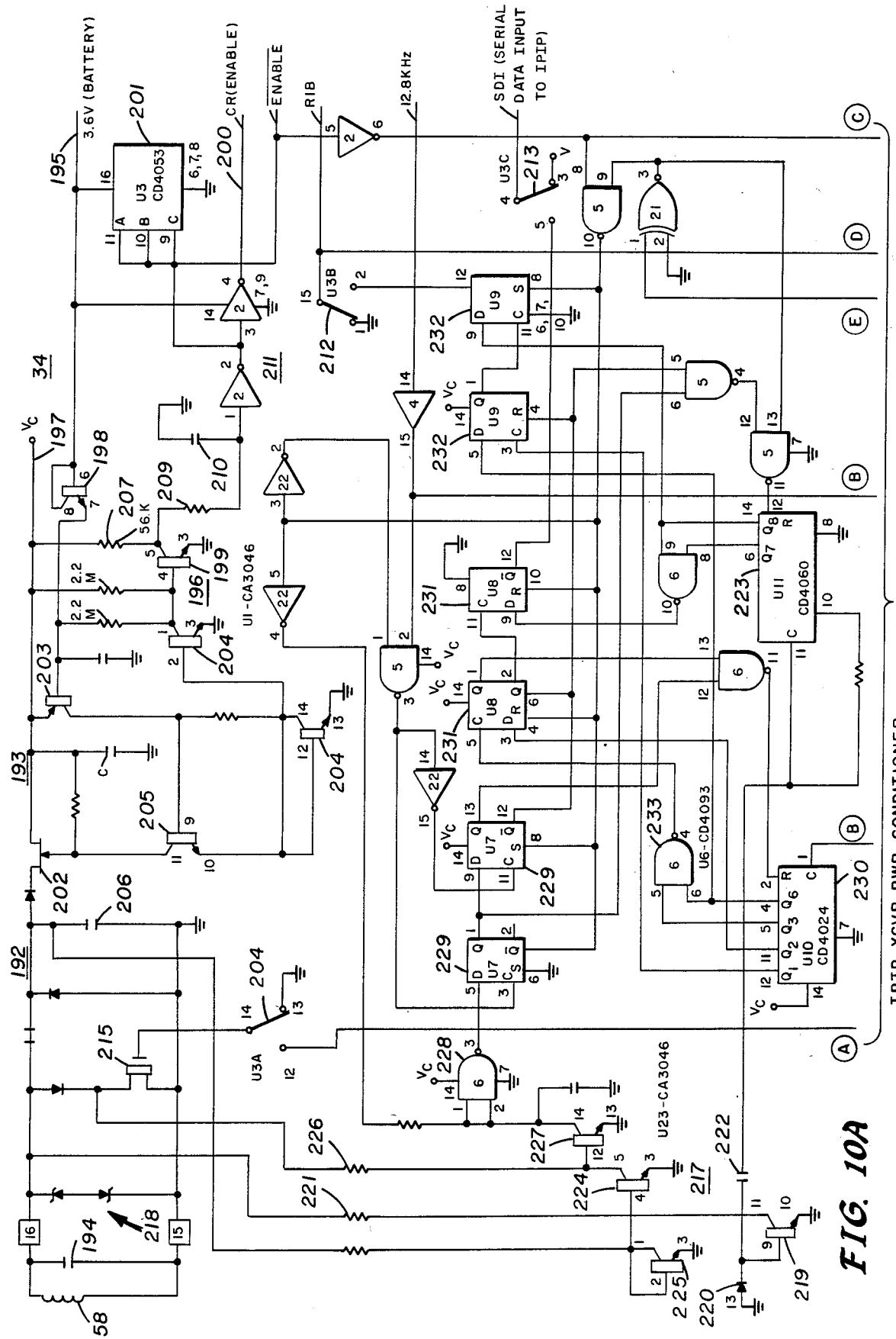
FIG. 10A is a breadboard schematic of the IPIP transceiver power conditioner and discriminators.
Figure 11:
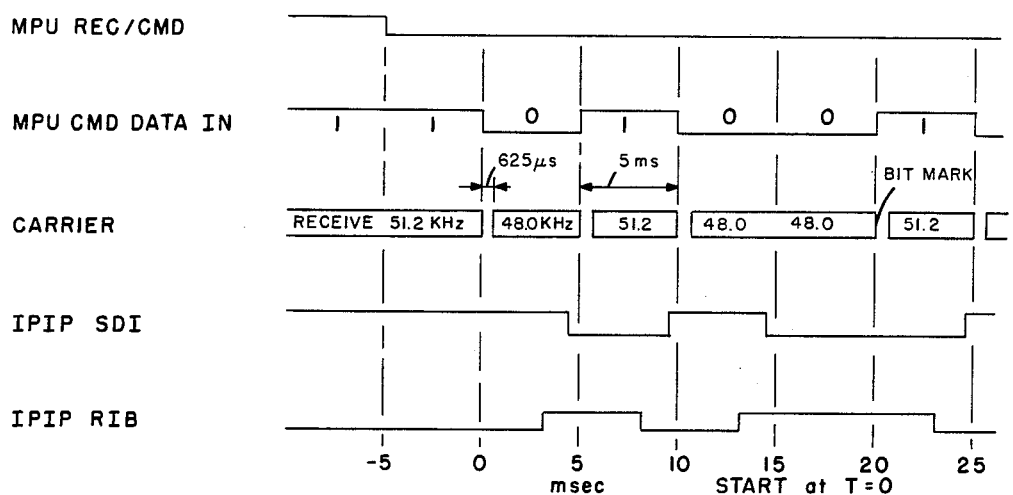
FIG. 11 is a timing diagram of a typical microprocessor data command.

Referring now to FIG. 10 a schematic of an IPIP transceiver breadboard embodiment 34 is presented for illustrative purposes only. The preferred embodiment has a majority of the digital circuitry incorporated into a single custom logic array. The voltage from the inductive link coil 58 is increased by a capacitive voltage doubler, shown generally at 192, then regulated by a voltage regulator circuit indicated at 193. Coil 58 is tuned by a 270 pF capacitor 194 which resonates considerably above the carrier frequencies so that it will not disturb the characteristics of the reflected impedance at certain ranges which would result in a subcarrier inversion during the return communication. The battery voltage, indicated as an input at 195 is used as a reference. The regulated line to the transceiver logic will be close to the battery voltage allowing direct interface of the logic levels. U1 indicated at 196, is an RCA five transistor array. When no communication link is present, the $V_c$ output 197 is zero. Transistor 198 is diode connected to the battery voltage 195, pin 7 of transistor 198 is about 0.6 volts below the battery voltage and current is always driving pin 4 of transistor 199 through the 2.2 Megohm resistor (the 1.5 microamp constant battery drain). During standby mode, pin 5 of transistor 199 stays at ground due to its 1.5 microamp base drive and also the zero volt $V_c$. This maintains the "CR" output 200 at zero volts and all the switches of U3, 201, at their standby level. JFET 202 is turned ON since it is not reverse biased but has no voltage to drive $V_c$. Transistor 203 and transistors 204 and 205 are all OFF. An external 51.2 kHz magnetic field causes a voltage rise at the drain of 202, which is an N channel JFET, which causes the 1 microfarad capacitor 206 to charge. Transistor 202 remains ON further charging capacitor 206 and raising the voltage $V_c$ 197 at the emitter of transistor 203. When the voltage $V_c$, 197, reaches the battery voltage 195 transistor 203 conducts causing the control loop to turn ON and back biasing the gate of 202 until voltage $V_c$ 197 is stabilized at the battery voltage 195. The 56 kohm resistor 207 has been drawing current as the regulator circuit 193 voltage $V_c$ comes up to the battery voltage. The first 3 or 4 microamperes through 203 drives the base of transistor 208 causing pin 1 of 208 to saturate turning transistor 199 OFF and allowing the network comprising the 56 kohm resistor 207 and 100 Kohm resistor 209 to charge up to $V_c$ as the 0.1 microfarad capacitor 210 voltage level rises. This removes about a 60 microamp load from the regulator circuit 193 and causes the "Enable"—"Clock Request" (CR) line 200 to go HI. A 15 mSec time constant (Resistor 209 and capacitor 210) driving the Schmitt trigger circuit, indicated at 211 and the hysteresis effect of removing the 56 kohm resistor 207 load provides noise rejection at maximum range. It also assures turn ON in the "Run/Idle TM" mode. Transistor 202 also provides circuit protection, i.e., $I_{dss}$ is about 200 microamps, in addition to being a series regulator for the normal maximum 80 microamp loads. The U3B switch, shown at 212, grounds the Run/Idle Bits (RIB) output when in standby. The U3C switch, shown at 213, sets the Serial Data Input to IPIP (SDI) line to the battery voltage. In addition, U3A switch, shown at 214, grounds the modulation VFET 215 to prevent it from draining any input energy. Input lines drive the U4 noninverting buffer 216 (FIG. 10B) which has no input protect diodes to its power line and can standoff the input signal HI when unpowered. The U23 CA 3046 circuit 217 contains the FM Limiter 218 (FIGS. 9 and 10A) and Bit Mark Detector 186 (FIG. 9) circuits. The signal from coil 58 is between about 5 and 32 volts peak to peak during operation, the upper value set by the two 1N4745 protection zeners, shown at 218. Transistor 219 and its phantom substrate diode 220 (FIG. 10A) provide hard limiting at ±0.6 V against the 200K drive resistor 221. The clipped signal couples through a 560 pF capacitor 222 to the amplifier input of a CD-4060 ripple counter 223. Ripple counter 223 counts incoming frequency any time its Reset line is low. The AM Bit Mark is detected by transistors 224, 225 & 227. Transistor 225 biases transistor 224 at a base voltage corresponding to a collector current proportional to about 0.66 the carrier peak voltage. Any coil input voltage greater than 0.66 the peak value causes pin 14 of 227 to saturate and U6 pin 3, shown at 228, to go HI. This tracking of input voltage level improves noise immunity during the BIT Mark interval. A Bit Mark interval starts by turning transistor 227 OFF and thus setting pin 3 at 228 LO. When in receive mode (assumed in this discussion) the U7, shown at 229, Q outputs will go LO as the clock pulses and the U10, shown at 230, timer counter Reset goes HI. When the carrier is turned back ON after the Bit Mark Interval, the outputs of U7, 229, go HI, the delay to U7-13 being between 78 and 160 microseconds. The U11-12 reset is accomplished during the 39 microsecond interval between U7-1 and U7-13 outputs going HI. This short interval minimizes the bias shift at the U11-11 input which occurs when the amplifier is gated OFF by the Reset input. Stray counts into U11 during the Bit Mark interval are not harmful since U10 is maintained Reset and no clocks are produced. Both U10 and U11 resets terminate at the same time on an inverted 12.8 kHz clock transition so that the first count into U10 occurs 39 microseconds later with all following counts at 78 microsecond intervals. The U10 timer 230 and the U11 counter 223 service two digital discriminators U8, shown at 231, and U9 shown at 232. Discriminator 231 produces SDI bits at U8-12. Discriminator 232 produces RIB bits at U9-12. The count interval for discriminator 231 is determined by the level output of U6-4 (LO), shown at 233, and a following clock output from U10-11. The count interval for discriminator 232 is set by U10-4 going HI followed by a U10-12 HI for a clock. The time detected by either of those events strobes the D input of the following flip-flop as shown in TABLE I. It is to be noted that when bit marks occur every 3.75 mSec the U8 binaries never strobe and ignore the higher speed FSK. To maintain this transparency at the end of the high speed R/I command sequence, the frequency must return to 51.2 kHz and one additional Bit Mark be transmitted. SDI is held at the "1" level (51.2 kHz) except during SDI data transfer which begins on its transition to a "0". The U10 and U11 ripple counters 230,233 draw significant current when running during receive, especially U11 which counts the carrier frequency.

TABLE I

| | CHARACTERISTICS OF IPIP DIGITAL DISCRIMINATORS | | | |
|---|---|---|---|---|
| count time | 51.2 kHz | 48.0 kHz | Decision Count | Margin |
| U8(SDI) 3.906 msec | 200 counts | 187 counts | 192 counts | +8,−5 |
| U9(RIB) 2.578 msec | 132 counts | 124 counts | 128 counts | +4,−4 |

Both counters are held reset during the transmit mode reducing the link power drain to 11 microamps from the 23 microamps used in receive.

As discussed above, there are four IPIP transceiver modes; Standby, Run/Idle Telemetry, Receive and Transmit. The Standby mode is defined as $V_c$ being less than the battery voltage and the "Clock Request" (CR) line low. When a communications link is established there will be a delay between $V_c$ regulation and "Enable" and "Clock Request" to insure start up in the Run/Idle Telemetry mode by setting the appropriate binaries. The Run/Idle mode is controlled by pin 13, flip-flop U17, shown at 234, (FIG. 10B), which takes precedence over $\overline{RTS}$ (Ready to send NOT) which is the microprocessor control of Receive/Transmit. The U17-13 is set by U21-10, at 235, during the startup interval. U17-13 is also set by a clock from the "RIA" line if a Run/Idle command is completed during normal receive operation, automatically shifting the transceiver to the R/I TM mode. U-17-13 drives switch U19B, shown at 236 and switch U19C, shown at 237. U19 is shown at 238. U19C HI connects U19A (control input for the output modulation frequency select switch) to the U14-3 R/I TM transmit format generator 239. U19C LO connects U19A to binary U17-1, shown at 240, which synchronizes the microprocessor output data to the transmitter 1.6 kHz subcarrier thereby providing synchronized switching between 3.2 kHz and 1.6 kHz when the bit values change. This synchronization is inherent in R/I TM since the format generator is driven from the same U12 ripple counter 241 that produces the two subcarrier frequencies. U19B HI connects the A control of U18, at 242, to the 320 mSec square wave out of ripple counter 241. U18A is the Receive/Transmit control, the transceiver goes to transmit mode if HI or receive mode when LO. The U18A pins 12, 13 and 14, shown at 243, define a switch which grounds the gate of the FET modulation switch 215 during receive and connects it to the U19A modulation select switch 244 during transmit. The control line U19-15, at 236 causes continuous Reset of the receiver counters 230, 223 during transmit, as discussed above, and clamps the discriminator 229, 231, 232 binaries to their standby states during the transmit mode. The transceiver switches back and forth between receive and transmit every 160 mSecs during R/I TM mode as controlled by U12-1. See FIG. 12 which illustrates the timing diagram for U18-14. Transmit begins when U12-1 goes HI and always starts with a 45 mSec preamble as shown in FIG. 12. This is to allow the external coherent FSK detector to lock on. The sequence is generated by U14, at 239, and U13 at 245. The latch implemented by the two U15 gates 246, 247 and the U13-4 output drive the U14 switch as illustrated in table II.

TABLE II

| Time | U14-A | U14-B | U14-3 | Subcarrier |
|---|---|---|---|---|
| 0 | 0 | 0 | 1 | 1.6 kHz |
| 10 mSec | 1 | 0 | 0 | 3.2 |
| 15 | 1 | 0 | 1 | 1.6 |
| 20 | 1 | 0 | 0 | 3.2 |
| 25 | 1 | 0 | 1 | 1.6 |
| 30 | 1 | 0 | 0 | 3.2 |
| 35 | 1 | 0 | 1 | 1.6 |
| 40 | 1 | 0 | 0 | 3.2 |
| 45 | 1 | 0 | 1 | 1.6 |
| 50 | 1 | 1 | "RUN" | "RUN" |
| — | 1 | 1 | "RUN" | "RUN" |
| 160 | 0 | 0 | 1 | OFF |

The notation "RUN" indicates the logic level of the "RUN" input signal U4-11, at 216. Between 160 and 360 mSec the transceiver goes to the receive mode. The transceiver remains in R/I TM mode until the external signal stops it by sending 48.0 kHz (the link is always initiated with a 51.2 kHz carrier) with a 3.75 mSec Bit Mark spacing during the receive portion of the cycle and for at least 140 mSec. This removes the reset from U16, at 246, allowing it to count the 25 Hz clock output from U12 and resetting U17 at a count of four, it is noted that the time is offset by 20 mSec as the first count occurs at 20 mSec after the start of receive. The transceiver will then go to either receive or transmit mode as selected by "$\overline{RTS}$". The R/I TM mode may also be interrupted if a R/I command is initiated during the receive portion of the cycle. The "$\overline{DR}$" (decoder runs NOT) line goes LO if the R/I command Decoder receives three correct key bits. U15-1, shown at 247, goes HI causing Reset of U12 until the command sequence has completed. "$\overline{DR}$" goes HI at the end of a successful command or when a command is aborted allowing the R/I/TM mode to resume. This provides a means to reset the microprocessor if the "$\overline{RTS}$" is held LO preventing normal receive operation. The IPIP 200 bps readout data has 8 cycles of 1.6 kHz or 16 cycles of 3.2 kHz per bit. These parameters are generated by requirements for the external equipment and different data rates and subcarrier parameters could be utilized with rates up to 1600 bps easily achieved. As can be appreciated, the discriminators 231, 232 are closely dependent on both the data rate and frequencies involved and must be redesigned for different input data rates. At the completion of communication, the link is broken either by removal of the external coil or the turn OFF of the carrier. The transceiver will coast for some time on its stored energy then revert to standby, switching the "RIB" output to permanent "0" and "SDI" to permanent "1". All logic power is removed except for U2 and U3 which monitor the U1 link detector 196 and control the output switches. The slow discharge of the 1 microfarad filter capacitors allows the "CR" request to drop out and the U3 switches to revert to standby position prior to the outputs reaching forbidden voltage levels.

Figure 7A:
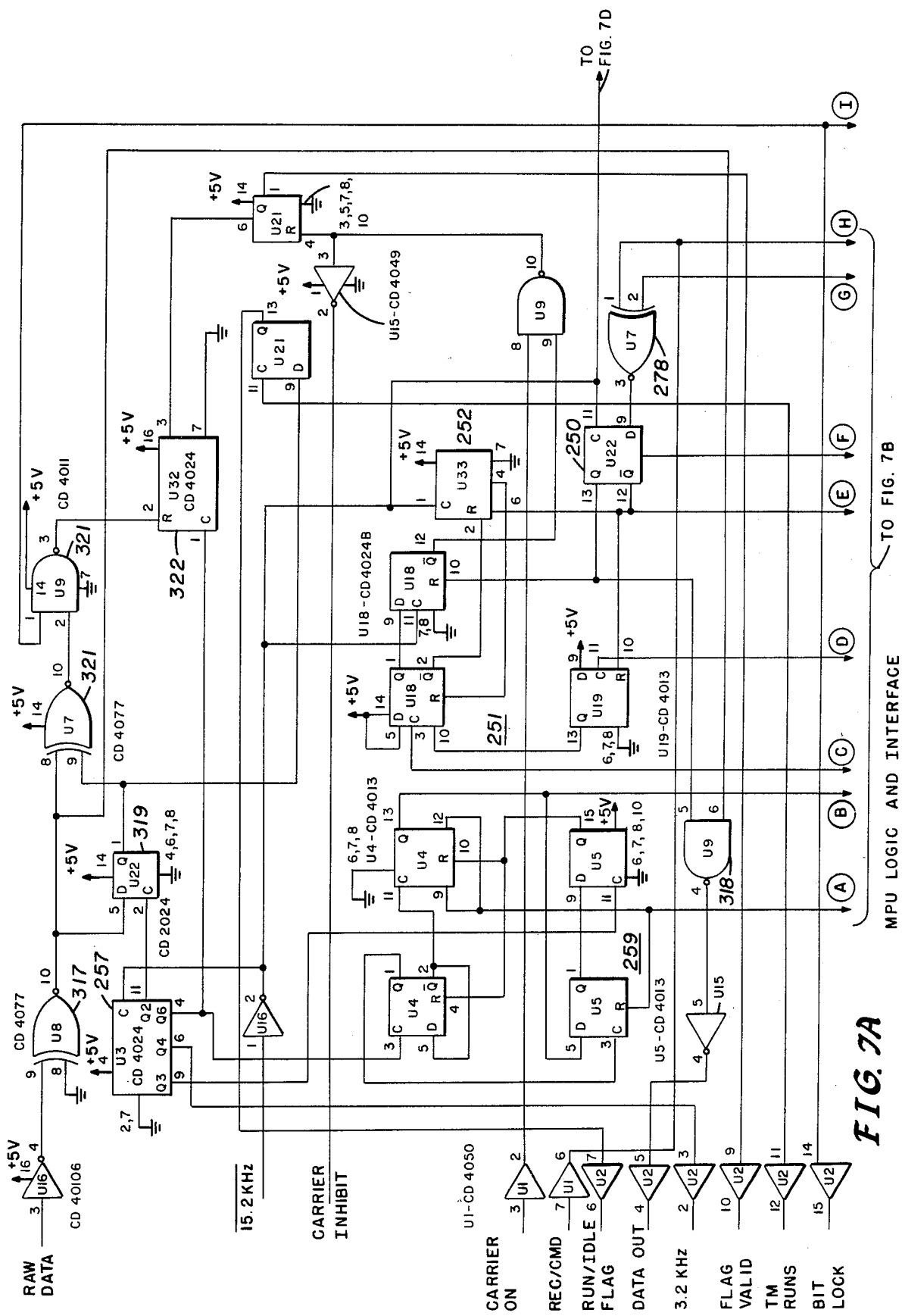
FIG. 7A is a schematic view of the MPU logic and interface circuits.
Figure 7E:
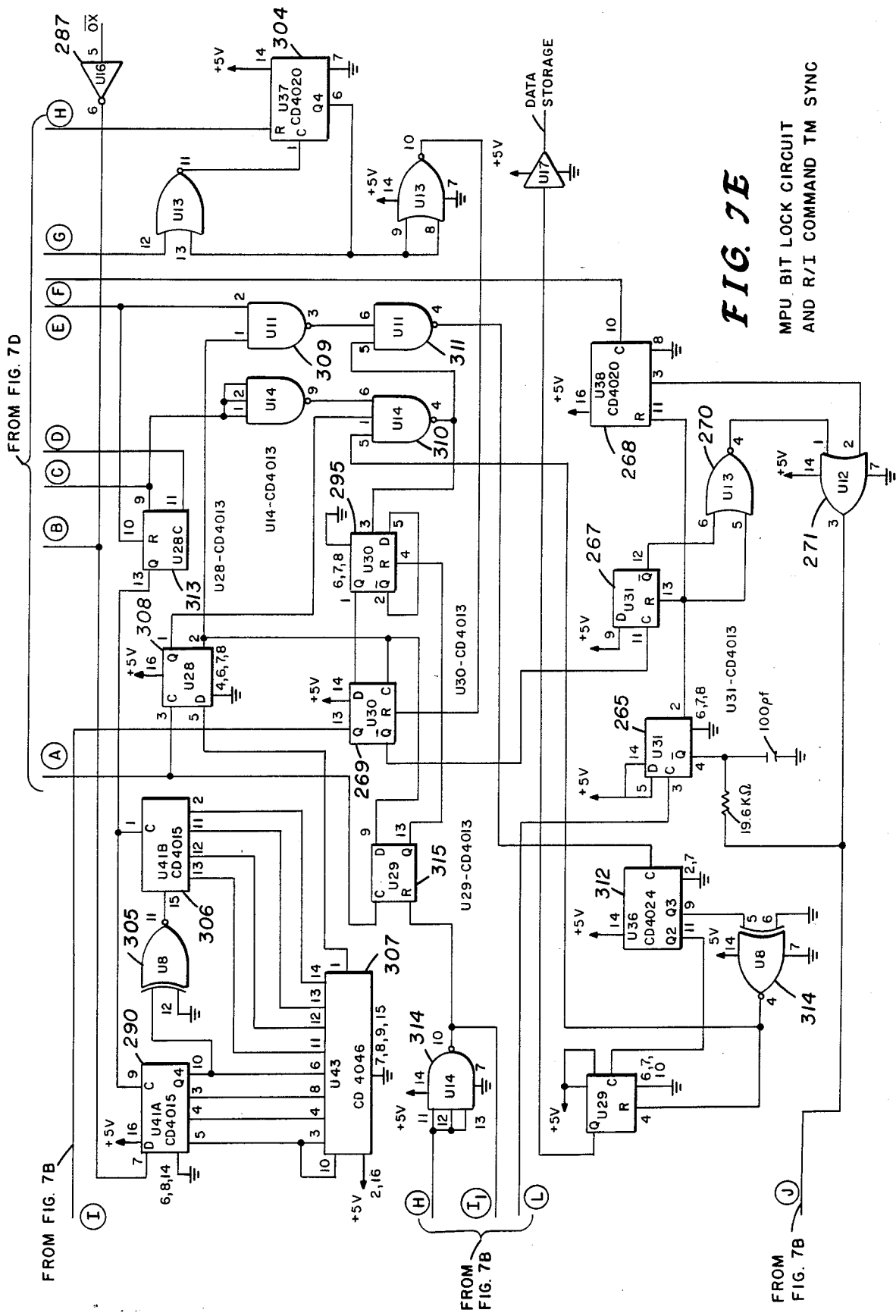
FIG. 7E is a schematic view of the MPU bit lock circuit and R/I command Tm sync circuits.
Figure 8:
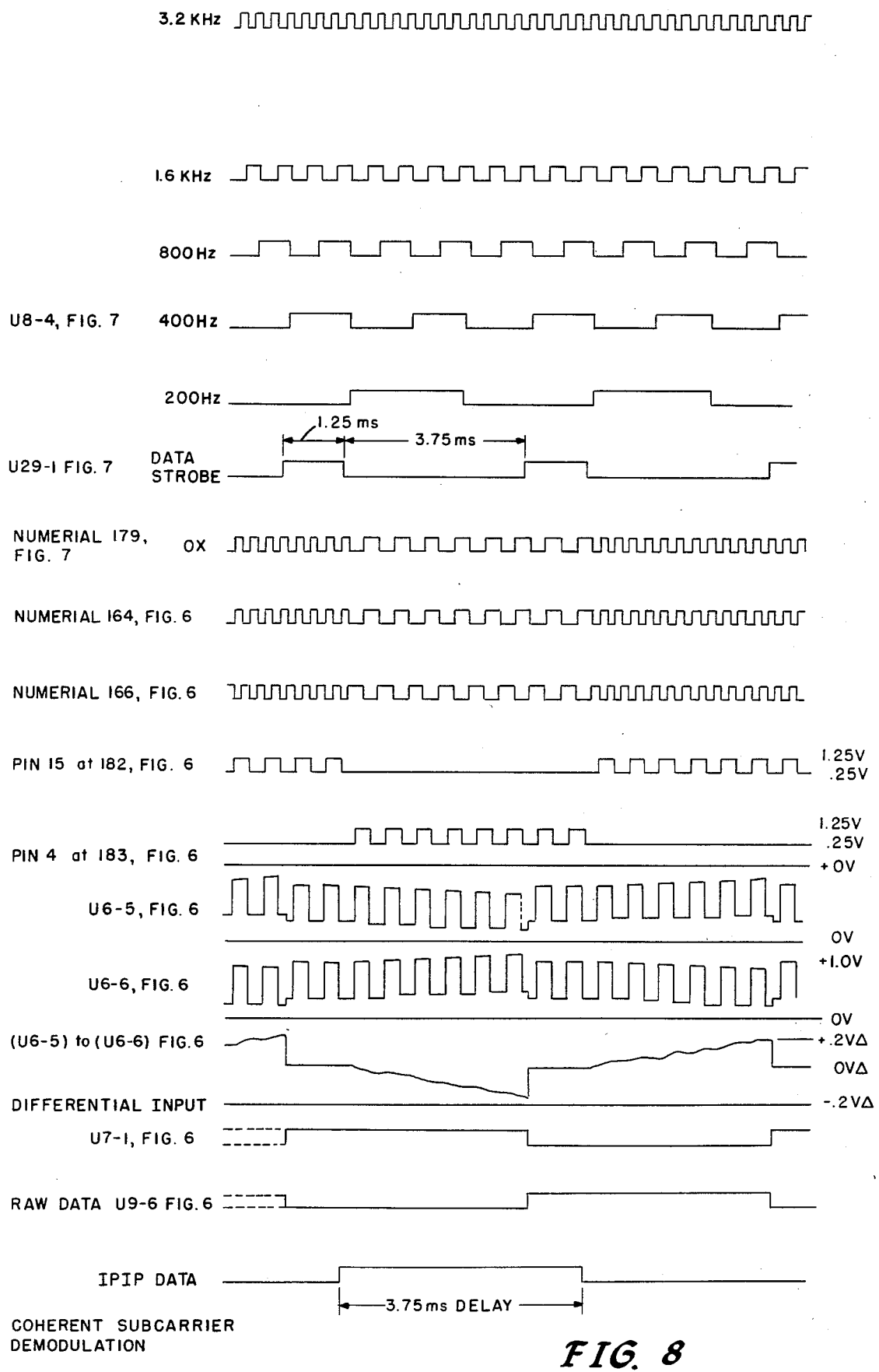
FIG. 8 is a timing diagram for coherent detection as utilized in the present invention.
Figure 13:
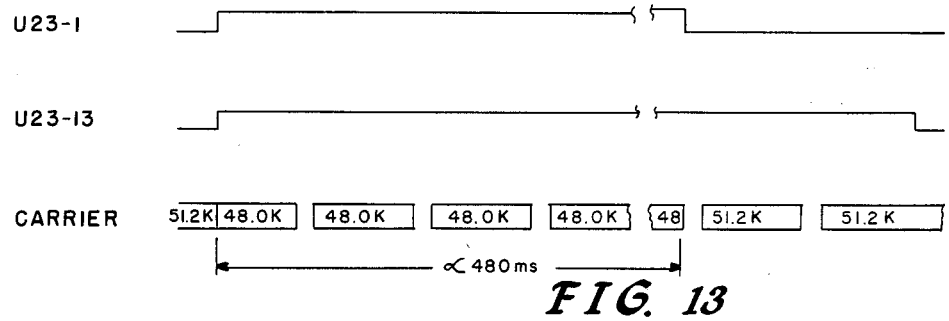
FIG. 13 is a timing diagram of the stop telemetry command timing.
Figure 14:
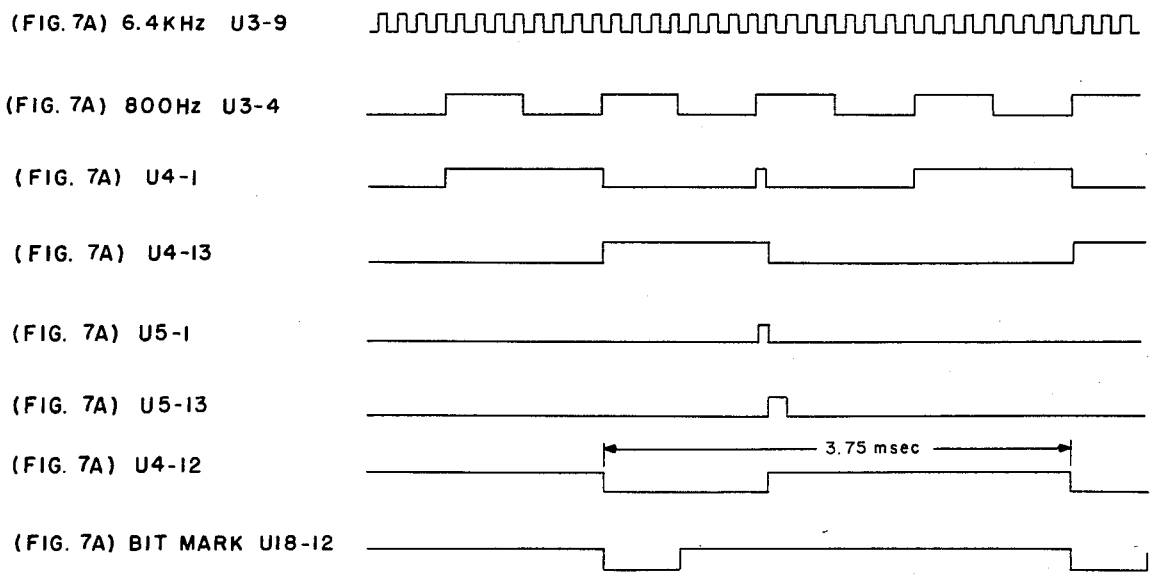
FIG. 14 is a timing diagram of the MPU 3.75 mSec generator timing.

Referring now to FIG. 7 and timing diagrams which will be specified during the following discussion the operation of the present invention will be further explained. FIG. 7 shows the relationship of FIGS. 7A-7E which are schematic diagrams of the MPU external transceiver digital board circuitry presented in five drawings for purposes of clarity. The IPIP implanted transceiver always comes ON in the Run/Idle Telemetry mode when first energized by an external communications link. The 320 mSec cycle alternates 160 mSec of status (i.e., Run or Idle) subcarrier with an 160 mSec listening period where it listens for a TM turn OFF command. This 320 mSec cycle is maintained until the communications carrier is removed which shuts off the IPIP transceiver, or a Flag TM Stop command is received. FIG. 12 shows the "Run/Idle Telemetry Format." U18-14 designates a switching point 243, FIG. 10 and the time trace indicates the subcarrier present on the communications coil 58 FIG. 10. Each cycle starts with 10 msec of 1.6 kHz to allow the external transceiver time to achieve frequency lock, followed by at least seven subcarrier frequency changes to insure bit lock. The remaining 115 msec of the transmit period has a fixed subcarrier frequency at either 1.6 kHz or 3.2 kHz indicating "IPIP Runs" or "IPIP is Idle", respectively. The external transceiver locks on to frequency, then bit timing during the preamble. It then checks for 79.6 msec at a fixed subcarrier frequency (Bit Lock HI) at which time the bit value is strobed to a binary flag and Bit Valid set HI. The external transceiver timing and phase lock circuits will be discussed below. As discussed above, a special rate of 3.75 msec per bit is used for the Run or Idle commands and the Flag TM OFF command which makes such commands independent of the IPIP microprocessor discriminator which decodes bits approximately 3.906 msec after Bit Mark time. These commands are always followed by an extra Bit Mark interval and 51.2 kHz output since the IPIP receiver digital discriminators begin counting at the end of Bit Mark. The IPIP microprocessor discriminator (line SDI, FIG. 10) must maintain a "1" output (51.2 kHz detected) at all times except when communicating with the microprocessor. Flag TM OFF, FIG. 7C, is a fixed 48.0 kHz coil drive with Bit Marks inserted every 3.75 msec, lasting 480 msec, see FIG. 13. The duration insures that one complete "receive half-cycle" at IPIP is stimulated since there is no timing sync for this command. The sequence is initiated when control line "Flag TM OFF" makes a positive transition. Data line "Command Data" FIG. 7B stays LO to insure the 51.2 kHz at the end of command. When line "Flag TM OFF" goes HI, pin 1 of U23, at 248, FIG. 7C goes HI. U23-2 goes LO enabling the U10-10 output, 249, FIG. 7B. U23-13 is set HI resetting U22-13, at 250, FIG. 7A which allows the U18 and U33 Bit Mark generator, indicated at 251 and 252, FIG. 7A, to operate. U12-10, at 253, FIG. 7C, output goes HI switching U42A and B, at 254, FIG. 7B, driving U10-2, at 255, FIG. 7B, from U10-10, at 249, and clocking the Bit Mark generator 251, 252 from U15-6, 256, FIG. 7B. Referring to FIG. 14 the 3.75 msec fast bit timing is illustrated. The 3.75 msec fast bit time is derived from the 51.2 kHz clock by U3, U4 and U5, shown at 257, 258 and 259 FIG. 7A, respectively. U4-12 drives U39-10, 260, FIG. 7C, which times 128 intervals (480 msec). U4-13 positive transition drives Bit Mark Generator 251, 252 producing a 625 microsecond LO level on the Carrier Inhibit line, FIG. 7A, at the start of each 3.75 msec period. The 625 microsecond Bit Mark interval initiates on each positive transition at the clock input of U18, 251. U33 Reset goes LO and it times out 32 periods of the 51.2 kHz clock for the 625 microsecond interval. U33-Q6 going HI resets U18 completing the operation. It is to be noted that Flag TM OFF may be sent in either Rec or Cmd mode. U22-13, 250, FIG. 7A, normally prevents Bit Mark generation during receive by holding U18-10 HI. However, U23-13, 261, FIG. 7C, resets U22-13, 250, FIG. 7A, during the Flag TM OFF command. U22-17 also enables U10-3, 255, FIG. 7B, allowing it to go negative and the Modulation output, FIG. 7C, to go HI switching the carrier frequency to 48.0 kHz. U19-13, 262, FIG. 7B, is used only for Run/Idle Command and remains LO during Flag TM OFF command. U39-8, 260, FIG. 7C, going HI at 480 msec resets U23-1, 248, setting U10-9, 249, FIG. 78, HI, changing Modulation, FIG. 7C, to LO and the transmitted carrier to 51.2 kHz. Seven and one half milliseconds later U23-13, 263, FIG. 7C, is clocked LO returning the logic to normal receive operation. It is noted that this sequence generates two final Bit Marks each followed by 51.2 kHz and that one Bit Mark would be sufficient. The Flag TM OFF command is asynchronous with IPIP signals and is initiated immediately when line "CMD FLAG TM OFF", FIG. 7C, transitions HI. The 480 msec duration of 48.0 kHz output with fast Bit Marks insures the signal will be present for at least one TM receive interval at the IPIP. The TM OFF command is confirmed if the IPIP TM ceases and no Bit Lock flag is produced over the next 320 msec interval. The IPIP transceiver also goes to Flag TM mode immediately following acceptance of a Run/Idle command which is normally followed by a receive period at the external transceiver to verify proper command acceptance. A Flag TM OFF command would then follow to resume normal operations, or if no further communciation is required, the carrier may be turned OFF or the communication head removed from the proximity of the IPIP. A Flag TM OFF command puts the IPIP transceiver under the control of the IPIP microprocessor, which selects send or receive, until the link is broken or another Run/Idle Command is accepted. The IPIP transceiver RIB (Run or Idle Bit) output, FIG. 7B, uses 3.75 msec duration bits as described above. These bits drive the IPIP Command Decoder which detects a 32 bit sequence of unique format to Set or Reset its "RUN" flip-flop. RUN HI corresponds to the IPIP Run state, RUN LO corresponds to IDLE wherein clocking is removed from all circuits. The Idle state allows IPIP storage at very low current drain and also resets the microprocessor allowing a restart if a soft error occurs in the program.

The IPIP transceiver mode (transmit or listen) is controlled by the $\overline{RTS}$ input, FIG. 10, from the microprocessor except when Flag TM is running. The Run/Idle Command may be sent with IPIP in receive mode or Flag TM mode. FIGS. 15 and 16 show the timing for the Run or Idle Command. The command is formatted with four 3.75 msec short bits for each information bit. Each information bit is 15 msec in duration, starts with 3.75 msec LO, follows with two identical information bit levels, and ends with 3.75 msec HI. A Bit Mark interval is produced between each of the four segments. Total transmission time is 480 msec. The information bits alternate between a pseudo-random key code and all identical command bits. The first bit transmitted (an odd bit) is a key bit. All even bits are identical ("1" for RUN, "0" for IDLE). The odd bits are in the key word pattern 0001110110010100. The command is accepted (and verified by Flag TM) only after all 32 bits (128 3.75 mSec bits) are verified for value and timing. A Run or Idle Command, FIG. 15 and 16, may only be sent when the external transceiver is in the receive mode, i.e., "Rec/cmd" line, FIG. 7A, HI. The command is requested when "RUN/IDLE EXECUTE" line, FIG. 7B, goes HI, Run or Idle having previously been set by line "Run/Idle CMD BIT", FIG. 7B, which must remain fixed during the command. The sequence does not start immediately. "Run/Idle Execute," FIG. 7B, input sets U31-2, 265, FIG. 7E, LO removing the reset from U31, 267, FIG. 7E, and allowing U38, 268 FIG. 7E, to count. If the IPIP is producing Flag TM, U30-12, 269, FIG. 7E, goes LO when Bit Lock is achieved and HI when Bit Lock is lost during the Flag TM receive period. This switches U13-4, 270, FIG. 7E, and U12-3, 271, FIG. 7E, HI near the beginning of Flag TM receive when IPIP can decode the RIB inputs. A proper sequence to IPIP causes the Command Decoder to announce "Decoder Runs" after the fifth information bit, the DR line locks the IPIP transceiver in receiver mode for the remainder of the command. The initial synchronization insures the first five bits (60 mSec) occur during the normal receive interval. When IPIP is not in Flag TM mode U31-12, 267, FIG. 7E, remains HI. U38, 268, FIG. 7E, times out 640 msec after the Execute request (to allow time for sync if available) then drives U12-3, 271, FIG. 7E, positive, starting the command sequence. The positive excursion of U12-3, 271, FIG. 7E, clocks U19-1, 271, FIG. 7C, HI and resets U31, 265, FIG. 7E, after a 2 microsecond delay. U31-2, 265, FIG. 7E, goes HI resetting U31-13, 267, FIG. 7E, and U38, 268, FIG. 7E. U20-1, 272, FIG. 7C, is clocked HI on the next positive transition of U6-9, 273, FIG. 7B. U6, 273, is clocked by the 3.75 msc timing generator, 257, 258, 259, FIG. 7A. U6-11 and U6-12, 273, FIG. 7B drive U44, 274, FIG. 7B, producing the four increment information bit increment while U6-9 alternately selects the Key or Command Bit by driving U42-C, 254, FIG. 7B. U20-1, 272, FIG. 7C, clocks U19-13, 271, FIG. 7C, producing a single Bit Mark. U12-10, 275, FIG. 7C, switches U42A and B, 254, FIG. 7B, connecting the Bit Mark generator, U18-3, 251, FIG. 7B to U15-6, 256, FIG. 7B, and the Modulation line U10-2, 255, FIG. 7C to U10-10, 249, FIG. 7C. U12-10, 12, 11, 275 and 276, FIG. 7C are set HI removing the 48.0 kHz Inhibit. U40-14, 277, FIG. 7C goes LO allowing operation of the pseudo-random sequence generator. U7-2, 278, FIG. 7A, goes LO, U7-3, 278, goes LO followed by U22-13, 250, FIG. 7A, LO allowing operation of the Bit Mark Generator, U18-3, 251, FIG. 7B. U20-13, 279, FIG. 7C, is clocked HI 30 msec after U20-1, 272, FIG. 7C, which enables U-10-4, 280, FIG. 7B, allowing the U44-3, 274, FIG. 7B, output to drive the Modulation line. It also sets U44-1, 274, FIG. 7B, HI for proper format and enables U9-11, 281, FIG. 7B allowing 3.75 msec pulses to initiate Bit Marks. The U20-12, 279, FIG. 7C, line goes LO enabling the U34 counter, 282, FIG. 7C to time out the next 16 pulses from U6-3, 273, FIG. 7B, at which time U-19-4, 271, FIG. 7C is reset. The total interval of U20-13, 279, FIG. 7C, HI is 480 msec. The clock details are illustrated in FIG. 15.

The Run/Idle Command function can be summarized as follows. The transceiver sends a Run or Idle Command having alternating 16 key and 16 command bits. All 16 command bits are identical, "1" for Run or "0" for Idle. The key sequence is generated by a pseudorandom 4-bit shift register sequence using Exclusive OR feedback (U40, 277, FIG. 7C). Each of the total 32 bits is formatted into four 3.75 msec periods starting with a LO, followed by two identical information bits and ending with 3.75 msec of HI. Bit Marks are transmitted at the start of each 3.75 msec interval. Transmission is synchronized to the beginning of "IPIP receive time" when IPIP sends Flag TM. Transmission is delayed about 640 msec from the Execute positive transition when Flag TM is not running. The IPIP Command Decoder uses the format, timing, key code and repetitive command bits to perform a secure mode change at the end of a properly decoded command. The sequence takes between 480 and 1120 msec depending on the initial delay.

Referring again to the Figures the data transmission to the implanted IPIP microprocessor will now be discussed. Binary data for the implanted microprocessor is carried over the FSK link using 5.0 msec bits. The Bit Mark, i.e., 625 microsecond absence of carrier, is generated only when the incoming bit value on line "Command Data" FIG. 7B, changes. The input train on line "Command Data" is repeated at the IPIP transceiver SDI (Serial Data Input to Microprocessor) with a delay of 4.5 msec. FIG. 17 illustrates the command Data Timing at the external transceiver. FIG. 11 illustrates the timing at the IPIP transceiver. The data transmit mode is set by switching the "REC/CMD" line, FIG. 7A, input LO. U7-3, 278, FIG. 7A, goes LO followed by U22-13, 250, FIG. 7A, which removes the reset from U18-10, 251, FIG. 7A, allowing Bit Mark Generator operation. Switch control Inputs U42-10 and 11, 254, FIG. 7B, are LO unless a Flag TM OFF or Run/Idle Command is in progress. These normal LO's connect U10-2, 255, FIG. 7B to U16-12, 283, FIG. 7B, which is the "Command Data" input inverted and delayed about 10 microseconds. U18-3, 251, FIG. 7A is switched to U15-10, 284, FIG. 7B, which is driven by the Exclusive NOR U-7-11, 285, FIG. 7B, which is an edge detector with a 10 microsecond output pulse, set by the resistor-capacitor network 286. This triggers the Bit Mark Generator 251, 252, FIG. 7A, every time the "Command Data" input changes value. The advantages of this are that the transceiver uses no absolute timing, the control computer times the 5.0 msec bit intervals, and a minimum number of Bit Mark intervals are transmitted. It is noted that this varies from the discussion above in that the Run/Idle and Flag TM STOP commands send a Bit Mark every 3.75 msec to prevent interaction with microprocessor SDI line.

The 200 bps microprocessor data transmission is summarized as follows. "REC/CMD" line, FIG. 7A, is set LO for "CMD" mode at which time the 48.0 kHz Inhibit, FIG. 7C, is removed and "Command Data" line, FIG. 7B, directly controls the output frequency. The Bit Mark generator is enabled and triggered from an edge detector to produce a 625-microsecond "Carrier OFF" period each time line "Command Data" changes. No bit timing is required in the transceiver, the output frequency is switched directly by the "Command Data" level. Routine operations require the transceiver to alternate between receive and command to accomplish "hand-shakes" with the implant, confirming data transmission followed by entering the new parameters into microprocessor RAM. "FLAG TM OFF", FIG. 7C, and "RUN/IDLE EXECUTE", FIG. 7B must remain LO during data transmissions. Flag TM OFF would execute normally and interrupt any data being processed. "Run/Idle Command", FIG. 7B, will not work (U7-3, 278, FIG. 7A would go HI inhibiting Bit Marks) but will still interrupt data transmission.

The receive control circuits will now be discussed in conjunction with the Figures. The external transceiver digital board, FIG. 7, contains frequency lock circuitry which generates coherent 1.6 and 3.2 kHz clocks for coherent detection of the IPIP subcarriers. They must lock on each time the IPIP goes into transmit mode and a subcarrier appears at the OX (Zero Cross) line, FIG. 7E. Each data transmission from the IPIP starts with 10 msec of 1.6 kHz subcarrier to allow digital phase lock at the external transceiver. The phase lock circuit aligns the coherent 1.6 kHz output with the negative transition from the OX output. The 1.6 kHz must be present for the initial lock as the 3.2 kHz subcarrier has two negative transitions during a 1.6 kHz period and phase lock might have a 180-degree error. The $\overline{OX}$ input, FIG. 7E, is inverted by U16-6, 287, FIG. 7E, then drives U25-9, 288, FIG. 7D, U27-5, 289, FIG. 7D, and U41-7, 290, FIG. 7E. U25 FIG. 7D is part of the frequency lock circuit, U27-5 provides lock detection, U41, 43 etc. are used to obtain Bit Lock once initial frequency lock is obtained.

Figure 18A:
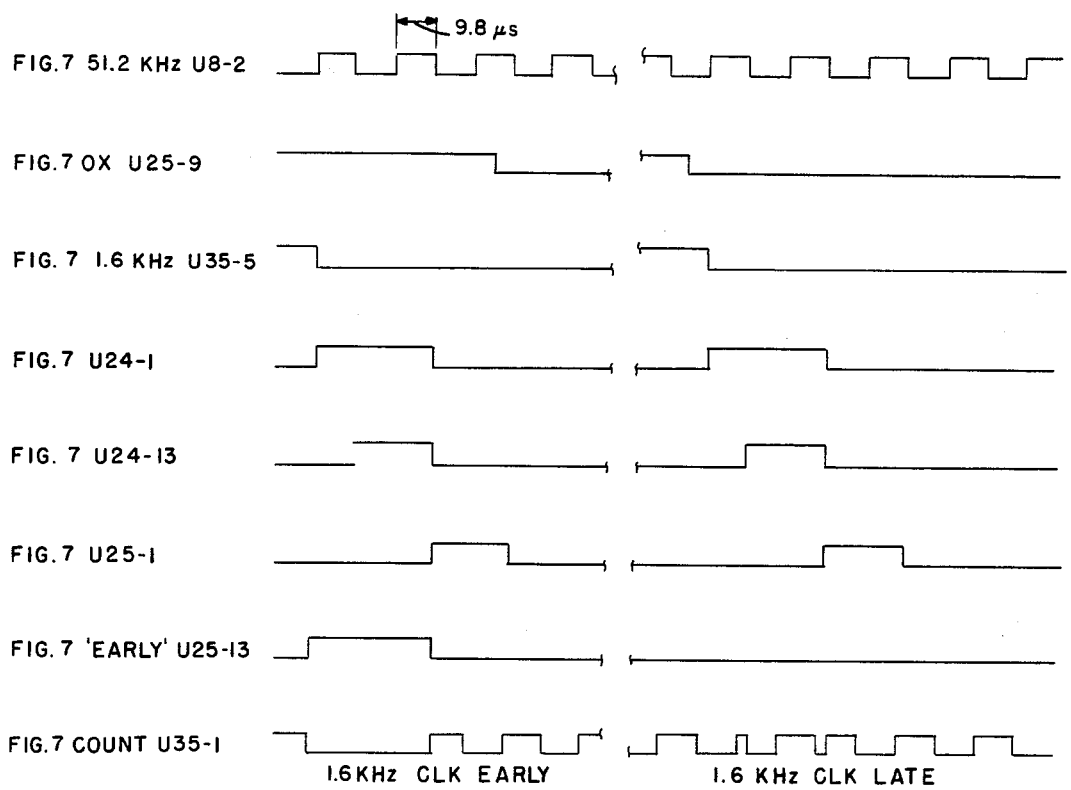
FIG. 18A is a timing diagram of the MPU frequency sync timing
Figure 18B:
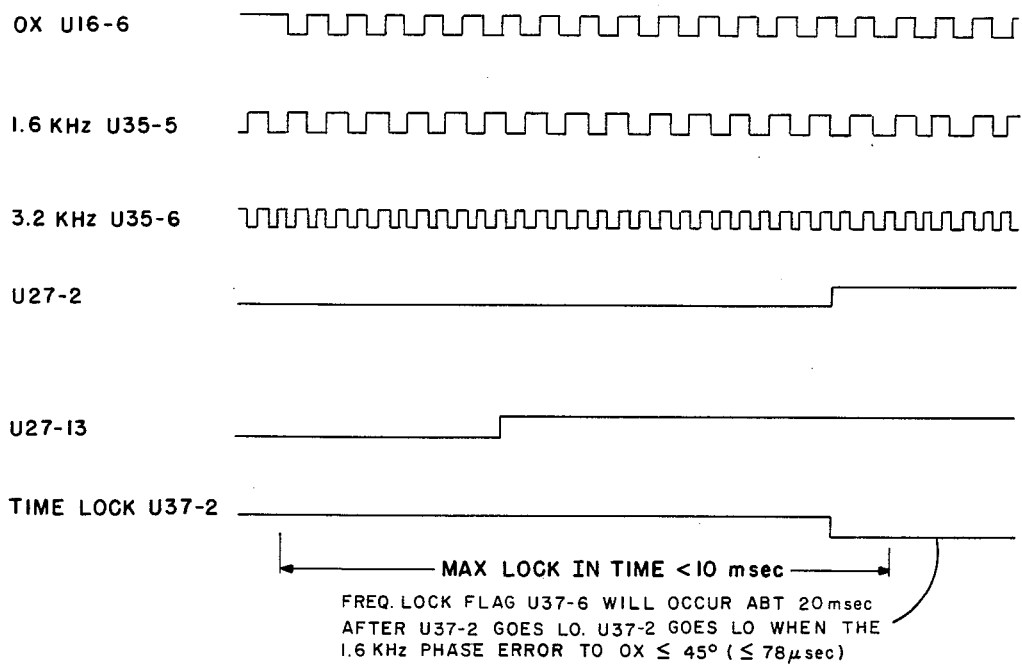
FIG. 18B is a timing diagram illustrating the MPU frequency sync sequence.
Figure 19:
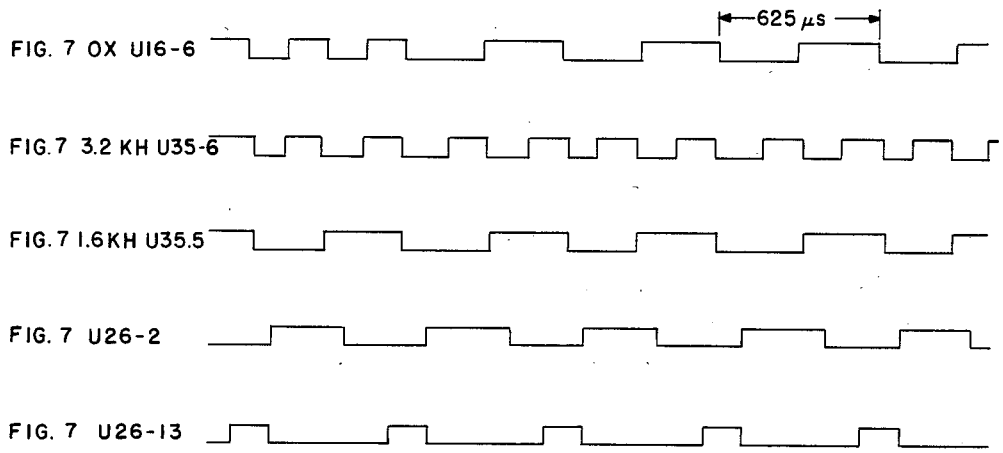
FIG. 19 is a timing diagram of the MPU frequency lock detection.

The coherent clocks are generated by U35, 291, FIG. 7D, from the "51.2 kHz" input, FIG. 7A, U35-5 provides the coherent 1.6 kHz and U35-6 provides the coherent 3.2 kHz. The negative transition of U35-5 is inverted at U11-11, 292, FIG. 7D, strobing U24-1, 293, FIG. 7D, HI and strobing the OX level into U25-13, 288, FIG. 7D. (FIG. 18 is in illustration of the associated timing diagrams.) One half clock period later, approximately 918 microseconds, U24-13, 294, FIG. 7D, is strobed HI. If OX is HI when U35-5 drops LO, U30-1, 295, FIG. 7E, is HI disabling the clock into U13-2, 296, FIG. 7D and keeping U35-1 LO. The next full clock period (19.5 microseconds) U25-1, 297, FIG. 7D, is strobed HI resetting U24, 293, 294, FIG. 7D. The U25-2 output is delayed about 2 microseconds by the resistor-capacitor network at 298 then inverted by U16-8, 299, which resets U25-13, 288, restoring the normal clock input to U35, 291. One clock pulse has been skipped and the coherent outputs delayed by 19.5 microseconds. OX LO at the U35-5 transition causes an extra clock pulse and advances the coherent outputs by 19.5 microseconds. In this situation U13-3, 296, FIG. 7E continues to operate normally. U24-12, 294, going LO changes the Exclusive OR U8-3, 300, from a noninverting to an inverting buffer which occurs about 2 microseconds after the clock transition. U8-3 changes back to a noninverter after the next clock period when U25-1, 297, resets U24, 293, 294. The clock to U35, 291, now has two negative transitions during one clock period which advances the count by 19.5 microseconds. This is shown in FIG. 18. The frequency lock circuit continuously dithers back and forth 19.5 microseconds at each clock period. Once lock is achieved, the worst case error is 19.5 microseconds or about 10 degrees at 1.6 kHz. The dither has an average value set by the difference in absolute frequency between the IPIP 12.8 kHz oscillator and the external transceiver 12.8 kHz divided down from the 51.2 kHz oscillator. The average error is small since the oscillators are accurate to better than 0.05%. Since the 1.6 kHz coherent frequency may be at any phase initially with respect to the received subcarrier, the worst case to achieve lock (phase error 180 degrees) with the adjustment rate of 19.5 microsecond per 1.6 kHz period would require 16 periods or 10 millisec. Frequency lock is verified prior to establishing Bit Lock. The U26 binaries, 301, 302 FIG. 7D, produce strobes at 45 degrees and 315 degrees of the 1.6 kHz coherent reference frequency which strobe the OX level. U27-2, 289, FIG. 7D, represents OX at 45 degrees and should be HI, U27-13, 303, stores OX at 315 degrees and should also be HI. Both levels must remain HI for 20 msec to remove the reset of the U30-13, 269, FIG. 7E bit detector. U37-6, 304, FIG. 7E is defined as the Frequency Lock Flag. The timing is shown in FIG. 19.

Figure 20:
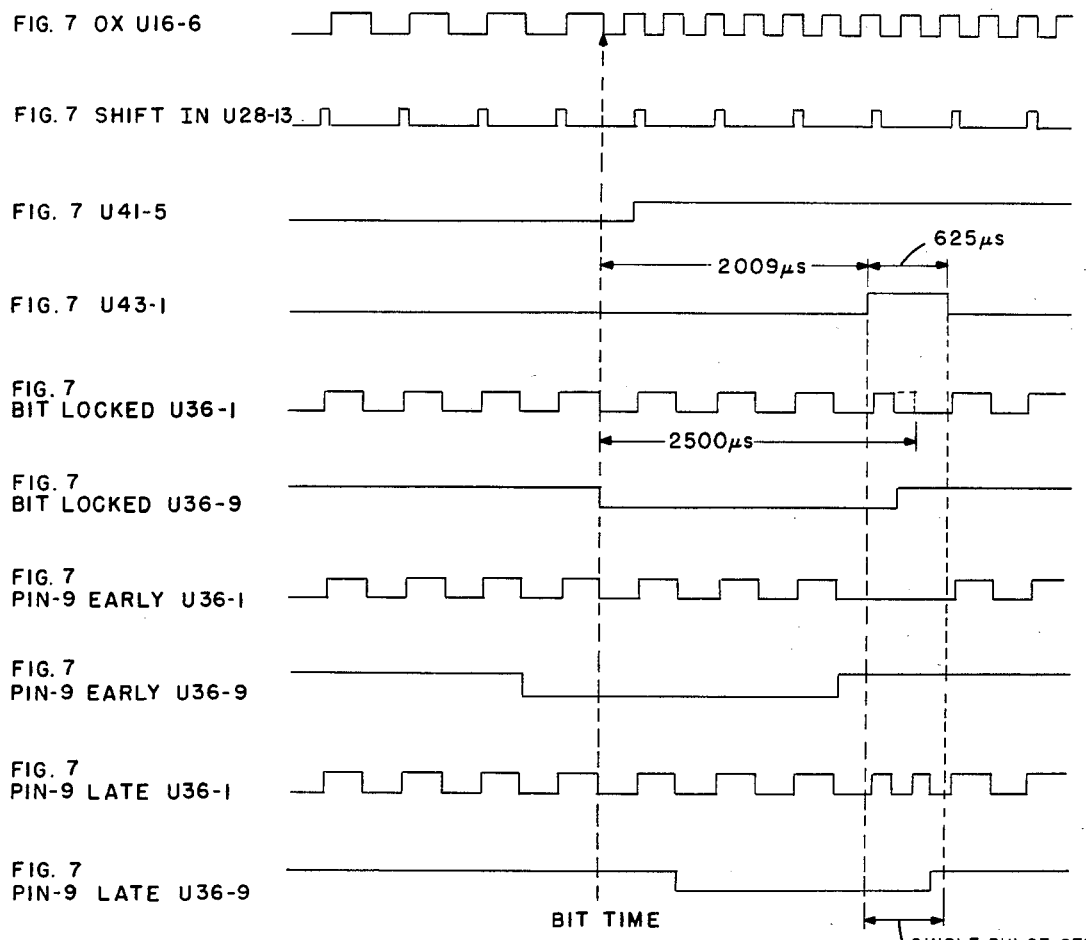
FIG. 20 is a timing diagram of the MPU bit lock timing.
Figure 21:
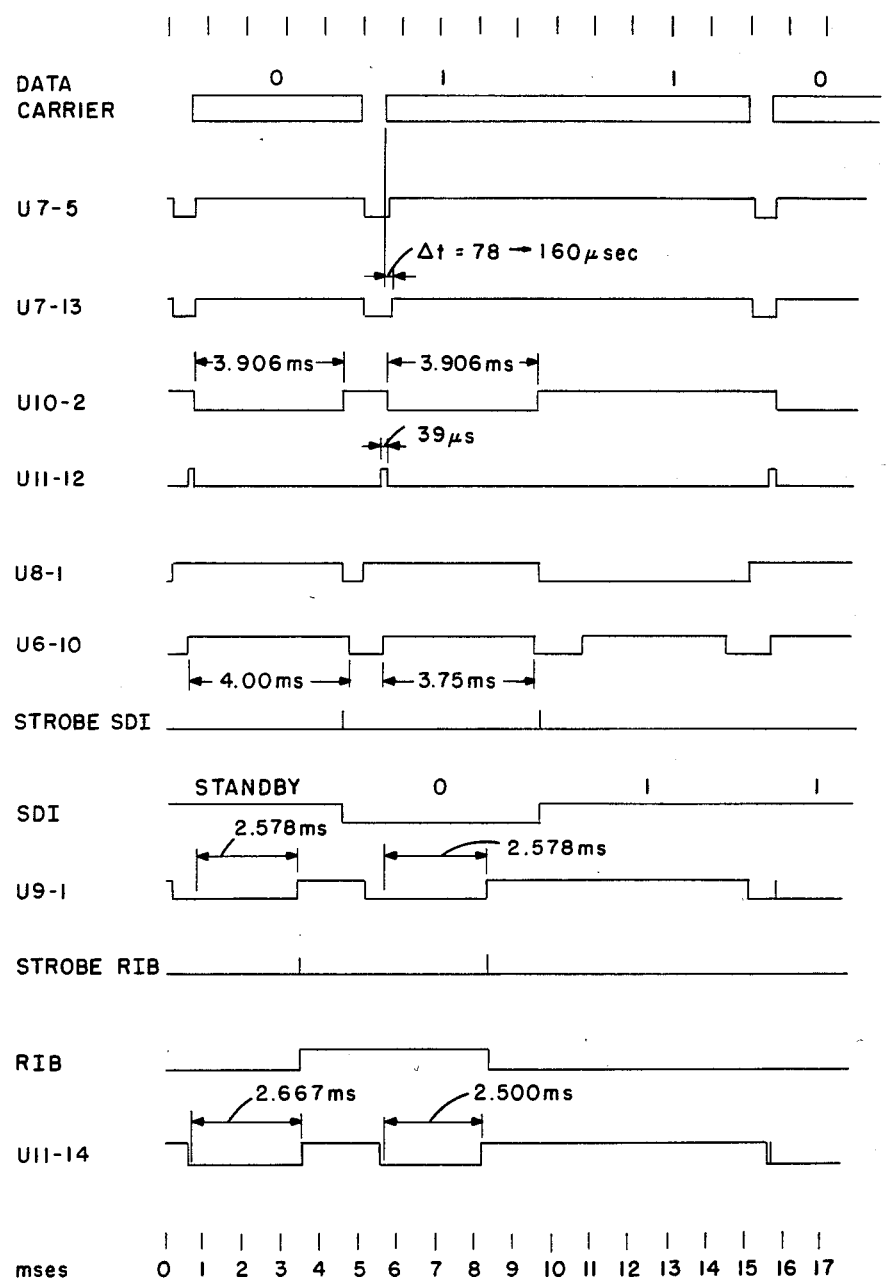
FIG. 21 is a timing diagram of the IPIP receive timing.

Bit phase lock is required for the coherent detector and is provided by the Bit Lock Circuit which will now be discussed. Bit phase lock allows integration over each bit interval independently of previous data. Bit lock is achieved after frequency lock by checking the OX line for time of subcarrier frequency change. OX is strobed into the U41A, 290, FIG. 7E, four bit shift register at 135 degrees of the coherent 1.6 kHz. The U41A register output is inverted by U8-11, 305, and shifted into the second U41B register 306. The outputs of all eight shift register stages are identical only between the fourth and fifth shift clocks following a change in subcarrier frequency. Bit lock timing is illustrated in FIG. 20. U43, 307, FIG. 7E is a complex gate network with pin 1 HI only when all eight input lines are identical. U28-1, 308, is clocked HI 19.5 microseconds later, disabling the U11-3, 309, gate and enabling the U14-6 gate 310. Output from the U11-4 gate 311 is a 1.6 kHz coherent clock used to drive U36, 312. U36-9 runs in sync with the bit time, its negative transition corresponding to bit change time. Bit lock phase is adjusted by checking the U36-9, 312, level during the 625 microsecond period that U43-1, 307, FIG. 7E, is positive following any subcarrier frequency change—on the fourth clock to U41, 290, 306, FIG. 7E, from U28-13, 313 FIG. 7E. U36-9 is inverted by U8-4, 314, FIG. 7E and drives the U14-6, 314 FIG. 7E, gate. If U36-9, 312, remains LO during the period U43-1, 307, is HI, no clock pulses pass through U14-6, 310, and the bit clock is retarded 624 microseconds. When U8-4, 314, is HI during the period U43-1, 307, is HI, two clock pulses occur, i.e., the 3.2 kHz is not gated to U36-1, 312, via U14-6, 310, and the bit clock is advanced 625 microseconds. When locked, U8-4, 314, changes 234 microseconds after U43-1, 307, goes HI gating U14-6, 310, off after allowing a single clock transition and no change in timing occurs. It is noted that the 19.5 microsecond dither associated with the coherent frequencies will sometimes dither the bit clock timing 19.5 microseconds if the average dither over the period is not zero, however, the 19.5 microsecond dither is trivial when compared to the bit clock 5000 microsecond interval. The maximum bit clock error is 2.5 msec. Four of the 625 microsecond correction increments will obtain bit lock. The preamble format at the beginning of every data transmission from the IPIP provides 10 msec for frequency lock, a steady 1.6 kHz subcarrier, followed by the data word "55" which has ten bit value changes. The bit clock produces a strobe at U29-1, 315, FIG. 7E, positive during the final 1.25 msec of each bit. A Bit Lock Flag, FIG. 7B, is used to indicate receiver lock for the control computer and to light an LED in the communications head. The U30-1, 295, FIG. 7E binary is reset to "0" by U29-13, 315, FIG. 7E, during the time U28-1, 308 is LO. Reset is removed during the U43-1, 307, HI interval and U30-3, 295, is clocked by the U14-6, 310 output. U30-1, 295, will be HI when U28-1, 308 goes LO only if it receives one single positive transition during the U28-1, 308, HI interval. U28-2 HI clocks the U30-1, 295, output into the Bit Lock Flag binary U30-13, 269. As a result, U30-13 is clocked LO if either zero or two clocks occur during the U28-1, 308, HI time. It is noted that U30-13, 269, is reset immediately if the Frequency Lock Flag U37-6, 304 FIG. 7E, goes LO. The Bit Lock Flag thus indicates (1) frequency lock has been achieved for at least the past 20 milliseconds and (2) the last subcarrier frequency change was synchronized with the bit clock.

The coherent detected data output is represented at "RAW DATA" FIG. 7A and is buffered by U16-4, 316, FIG. 7A and U8-10, 317, then used for the digital Flag TM check. U8-10, 317 also drives U9-6, 318 which is gated by U22-13, 250 to insure a LO output from U2-4 "Data Out" FIG. 7A, during command and data transmissions. Data at U8-10, 317 drives U22-5, 319 and U7-8, 320. U22-5 acts as a 78 microsecond delay clocked by 12.8 kHz from U3-11, 257, making U7-10, 320 an edge detector with a 78 microsecond output pulse. U9-3, 321, FIG. 7A, goes HI resetting U32, 322, any time Bit Lock is lost or U7, 320, detects a change in "RAW DATA." U32-3, 322, goes HI indicating TM data is present and valid only after Bit Lock HI and no subcarrier frequency change for 79.6 msec. The fixed bit time of Flag Telemetry transmit from the IPIP is 115 msec as illustrated in FIG. 12, RUN/IDLE Telemetry Format. U32-3, 322, going HI strobes U22-1, 319, into U21-13, 323, the "RUN/IDLE Flag." It also sets U21-1, 323, indicating "Flag Valid." U21, 323, remains set until a "Carrier Inhibit," FIG. 7A, is generated by either a "Flag TM OFF" command, "Run/Idle" command, or changing to command mode and sending a "0" bit. "Flag Valid" has a high confidence level since it requires Frequency Lock, Bit Lock and 79.6 msec of continuous subcarrier frequency. The external transceiver is normally turned ON in receive mode and Flag Telemetry will start as soon as the IPIP detects the 51.2 kHz carrier. Bit Lock confirmation by the LED in the communications head provides immediate feedback to the operator that the communications link is established, a 320 msec blink rate of the LED verifies that the IPIP has come up in FLAG TM mode.

Figure 22:
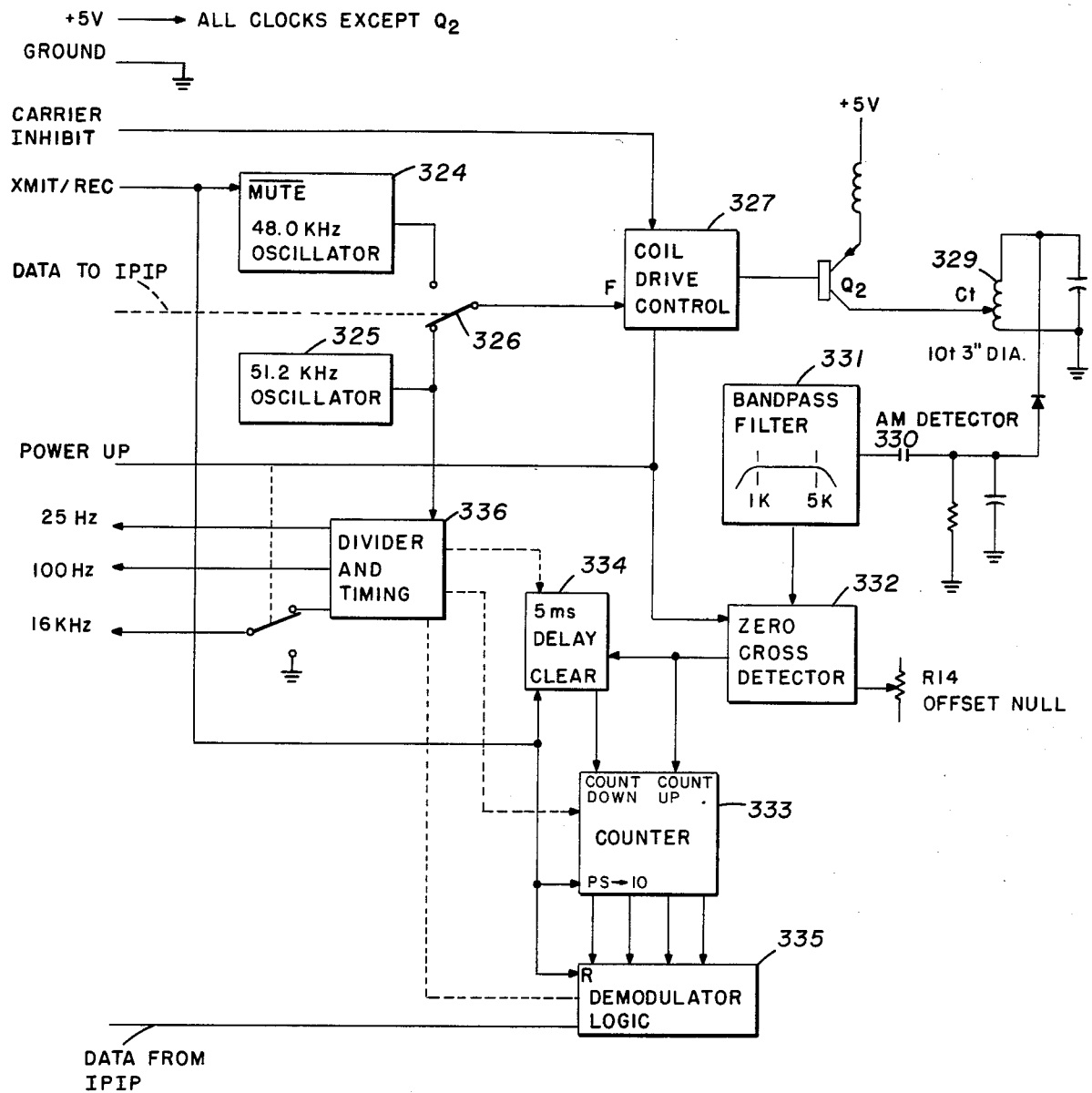
FIG. 22 is a block diagram of the PPU transceiver.
Figure 23C:
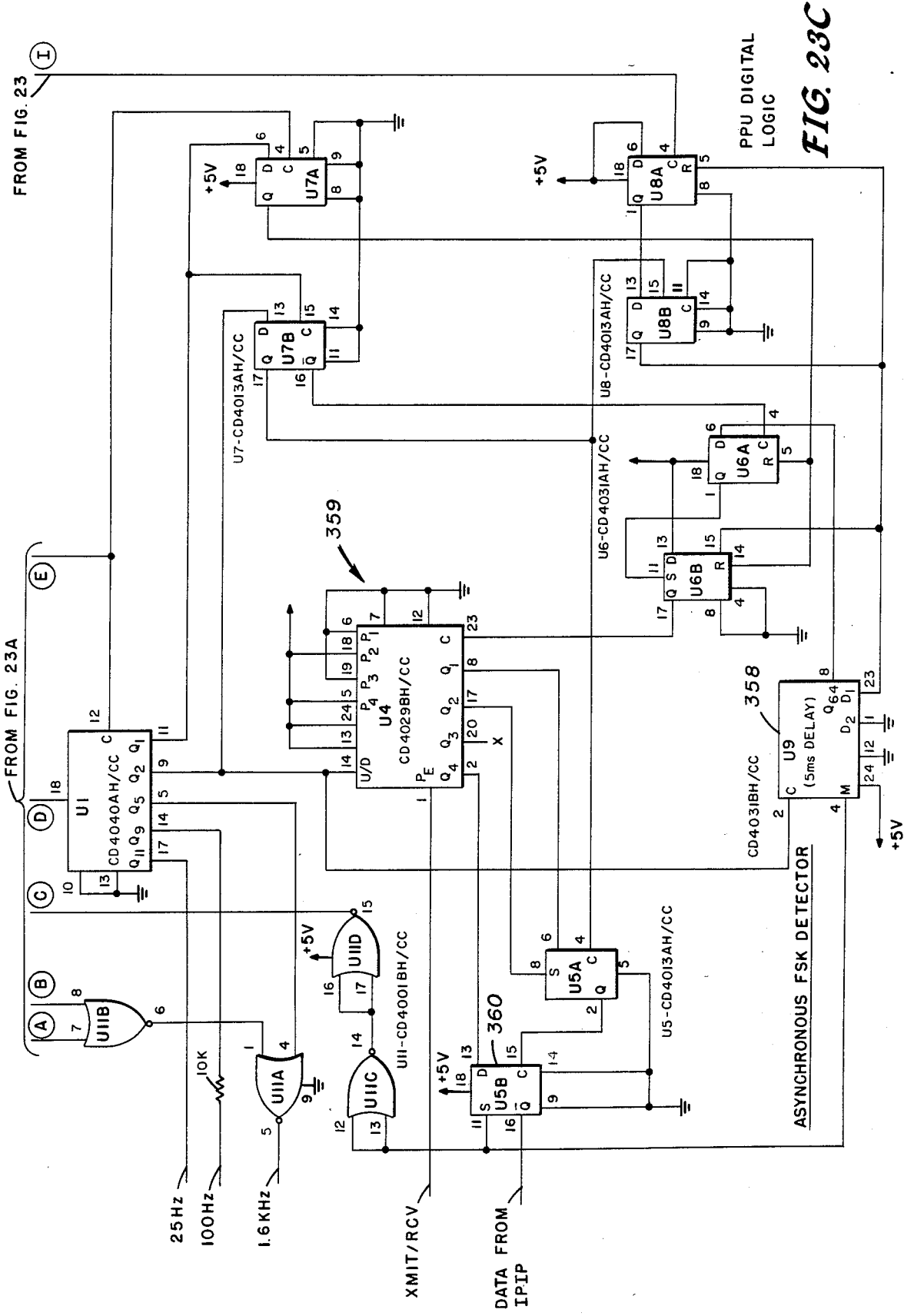
FIG. 23C is a schematic view of the PPU transcriver analog circuits.

Referring to FIG. 22, a simplified transceiver used for the patient's programming unit (PPU, 22 FIG. 1) will now be described. The transceiver portion of the PPU is shown in a block diagram in FIG. 22. The transmitter portion comprises a 48.0 kHz oscillator 324, a 51.2 kHz oscillator 325, a switch 326 to select a desired output from either oscillator 324 or 325 to drive coil driver 327 which in turn controls transistor 328 which drives coil 329. Impedance changes in the inductive field established by coil 329 and the IPIP coil causes an amplitude modulation of the coil voltage (described above). This amplitude modulation is detected by AM detector circuitry shown generally at 330. The output from AM detector 330 is throughput a bandpass filter 331 to a zero cross detector 332. The output of zero cross detector 332 is input to counter 333 and delay 334. Demodulator logic 335 receives an input from counter 333 and outputs data from IPIP. A divider and timing component 336 provides inputs to delay 334, counter 333, demodulator logic 335 and coil drive control 327 via switch 326. FIGS. 23–23C is a schematic diagram of an embodiment of the PPU transceiver. It is emphasized that the detailed description is for illustrative purposes only and the scope of the invention is to be construed only in conjunction with the appended claims. The inductive field for communication (at 48.0 or 51.2 kHz) is generated by the current circulating in coil 329 which is tuned by mylar capacitors 337 (about 0.5 microfarad) for equal amplitude at both frequencies. Transistor 328 drives the center tap of the coil with a shaped pulse that is timed by inductor 329 and the pulse width determined by the U2B input network indicated at 338. This results in a Class C stage with a good waveform. Power dissipation in transistor 328 is minimized by the pulse shaping with the voltage across the transistor minimized during current flow. The frequency of coil 329 is selected by U10A (FIG. 23A) at 339, from the two Schmitt triggers in U3, at 340, that buffer the crystal oscillators 341, 342. U10A is controlled by the input line "Data to IPIP". U10C, at 343, is controlled by the input "Power Up" and ties U3-15, (FIG. 23B) at 344 to +V if that signal is LO. U10B is controlled by input "Carrier Inhibit" and grounds U10-17 (FIG. 23B), at 344, if that line is HI. A carrier will be present if "Power Up" is HI and "Carrier Inhibit" is LO. The carrier will be at 51.2 kHz if "Data to IPIP" is HI, and 48.0 kHz if "Data to IPIP" is LO. The "Power Up" control is used to minimize current drain when no communication is requested. When "Power Up" is LO there is no coil drive, power is removed from the dual comparator U2, at 338, FIG. 23B, and the 1.6 kHz output to the digital circuitry is disabled. For minimum power drain, "Xmit/Rec" is held LO to disable the 48.0 kHz oscillator output. The input, "Carrier Inhibit", is used during data transmission to IPIP. A "Bit Mark" is generated at the start of each new bit by inhibiting transmission for about 625 microseconds. The timing is provided by the microprocessor in the digital electronics. The U2B comparator 338 drives transistor 345 as a switch causing current to flow in transistor 328 when U2-18 is LO. The RC input to comparator 338 inputs times the drive pulse to about two-thirds of the negative input duration. The topology also causes U2-18 to go HI (turning transistors 328, 345 OFF) whenever U10-17, at 344, is grounded for an extended period, i.e., "Carrier Inhibit" HI.

The ten turn communication coil 329, FIG. 23B, is driven at its center-tap allowing it to act as an autotransformer and the voltage across the coil is normally a sine wave of slightly greater than four times battery voltage (peak to peak). The extra voltage is due to the inductor 329 as the energy stored during the current drive adds to the voltage available from the battery. The center tap drive also reduces carrier waveform distortion since the stray inductance between coil halves isolates the tuning capacitor during current drive. The current driving the coil 329 is routed to the battery through separate leads to minimize the cross-talk to the high-impedance, low level, oscillators from the drive stage. The leads are run as a twisted pair for the same reason. Oscillators 340, 341 are high impedance circuits requiring proper layout and shielding to obtain optimum performance. A "Mute" input is made available so the 48.0 kHz oscillator 340 may be muted which prevents a phantom 3.2 kHz subcarrier in the receiver (beat note with the 51.2 kHz receive oscillator). As described above, data return from the remote IPIP modulates the receive carrier (continuous 51.2 kHz coil drive during receive operation) by shorting out the IPIP coil at a subcarrier rate of either 1.6 or 3.2 kHz which causes a low level AM on the carrier which is demodulated on the negative peak by the detector diode 347. A lowpass filter, made up of coils 348, 349 and capacitors 350, 351 further rejects the 51.2 kHz carrier. Low frequencies, such as power line hum and mechanical modulation due to movement, are eliminated by capacitor 352, then by the differential drive to the comparator 356 comprising capacitors 353, 354 and their associated resistors. The resulting bandbass is roughly from 1000 to 5000 Hz. Resistor 355 provides a vernier correction of the DC offset. Comparator 356 uses both DC and AC positive feedback to provide hysteresis and reject high frequency noise. The DC hysteresis is about 1 mV and sets the minimum level subcarrier detectable. AC hysteresis starts at 10 mV, decaying exponentially with about a 10 microsecond time constant.

Communication range in receive is slightly less than that for transmit with three inches being typical under low noise conditions. Subcarrier demodulation is accomplished by counting the number of zero-crossings from U2-2, at 356, during the previous five milliseconds. This is a continuous measurement requiring no bit time or synchronization information. Each positive transition at U2-2 causes U8-1, at 357, FIG. 23C to go HI. That count is synchronously strobed into the U9 delay shift register 358 (whose input occurs 5 msec later at U9-8) and also causes an immediate UP count in the U4 Up/Down Counter 359. The Up/Down counter total is dependent only upon its original state and the total input counts during the previous five milliseconds. The Up/Down counter 359 is preset to 10 during transmit. In receive, Up/Down counting runs continuously with the U2-2 (356, FIG. 23B) output. The two subcarriers are at 1.6 and 3.2 kHz or 8 and 16 counts per five millisecond interval respectively. If either subcarrier runs continuously the following is true: Counter 359 count for 1.6 kHz continuous equals two, count for 3.2 kHz continuous equals ten and counter 359 initial count when going into receive equals ten. Prior to receive, counter 359 is preset to ten and U5-16, at 360, to LO. Each data transmission from IPIP begins with ten milliseconds or more of 1.6 kHz as a preamble, described above, which is sufficient time for counter 359 to achieve a constant value of 2, i.e., 1.6 kHz continuous, independent of the number of random counts out of the receiver comparator between the time the receive mode started and the IPIP began subcarrier transmission. The clock synchronizing the above operation is at 12.8 kHz. Data bit value is determined by the state of U5-16, at 360, which is gated from Up/Down counter 359 using the following logic: data goes LO when counting upward and reaching 8 or 12 and data goes HI when counting down and reaching 4 or counting up and reaching 0. Thereby a minimum hysteresis of four counts is generated. If no noise count occurs the count will vary between 2 and 10 for 1.6 and 3.2 kHz input respectively requiring a change of 6 counts prior to changing value.

While the invention has been described with reference to the accompanying drawings, it is to be clearly understood that the invention is not to be limited to the particular details shown therein as obvious modifications and substitutions may be made by those skilled in the art. The invention should only be construed within the scope of the following claims.

What we claim is:

1. A communications link for communicating with a programmable medical device adapted to be biologically implanted in a living body, comprising:
   an internal receiver located in said programmable medical device;
   an external transmitter adapted to be located extracorporeal to said living body;
   means for establishing an inductive field between said external transmitter and said internal receiver;
   a modulation means, incorporated in said external transmitter, for frequency shift keying said inductive field and for superimposing bit marks on said inductive field, so as to transmit digitally formatted information;

a bit mark detection means, incorporated within said internal receiver, for detecting said bit marks in said inductive field;

a limiter and zero crossing detector means, incorporated within said internal receiver, for detecting the zero crossing of the inductive field;

a digital discriminating means, connected in association with said bit mark detection means and said limiter and zero crossing detector means, for counting the number of zero crossings of said inductive field for a preset interval after said bit mark to establish the frequency of the inductive field, wherein said frequency indicates the received binary digit.

2. A communications link, as recited in claim 1, wherein said means for establishing said inductive field between said internal receiver and said external transmitter comprises:

a first inductive coil provided in association with said external transmitter; and a second inductive coil operably coupled to said internal receiver wherein said inductive field is established between said first inductive coil and said second inductive coil.

3. A communications link, as recited in claim 2, further comprising:

means for generating a first frequency to represent a first binary digit;

means for generating a second frequency to represent a second binary digit; and means for selectively modulating said inductive field by selectively driving said first inductive coil in said external transmitter at said first frequency or at said second frequency resulting in a selectively modulated inductive field.

4. A communications link, as recited in claim 3, wherein said digital discriminating means comprises a first counter with gate duration set by a clock and a second counter, and wherein said first binary digit is associated with a first total zero crossing count for said preset interval and said second binary digit is associated with a second total zero crossing count for said preset interval.

5. A communications link, as recited in claim 4, further comprising means for selectively transmitting at least two channels of data over said inductive field, one channel having a slower data rate than the other, and each of said channels is digitally formatted at a different digital bit length, wherein the time lapse between bit marks establishes the digital bit length.

6. A communications link, as recited in claim 5 wherein said digital discriminating means further comprises a means for distinguishing between each of said channels based upon the time between bit marks.

7. A communications link, as recited in claim 6, wherein said means for distinguishing between channels comprises a plurality of discriminators, each of said discriminators is associated with a particular one of said channels and wherein said discriminator associated with the slower channel selectively identifies only digital bits having a bit length associated with said slower channel.

8. A communications link, as recited in claim 2, further comprising:

an internal transmitter adapted to be located in said programmable medical device and operably coupled to said second inductive coil, said internal transmitter comprising:

a coherent modulation means, for coherently generating two subcarrier frequencies and for switching, in accordance with digitally formatted information, between said two subcarrier frequencies during coherent waveform transitions of said two subcarrier frequencies, an impedance reflection means, operably controlled by said coherent modulation means, for selectively changing the reflective impedance of said second inductive coil in accordance with subcarrier frequencies selected by said coherent modulation means, thereby changing the impedance value of said inductive field, an external receiver means operably connected to said first inductive coil for detecting changes in the impedance value of said inductive field, caused by said impedance reflection means.

9. A communications link, as recited in claim 8, wherein said coherent modulation means comprises:

means for generating a first subcarrier frequency to represent a first binary digit;

means for generating a second subcarrier frequency to represent a second binary digit; and wherein said impedance reflection means selectively modulates said inductive field by said first subcarrier frequency or by said second subcarrier frequency, thereby producing a selectively amplitude modulated inductive field.

10. A communications link, as recited in claim 9 wherein said coherent modulation means further comprises:

means for continuously driving said inductive coil in said external receiver at a selected constant frequency.

11. A communications link as recited in claim 9, wherein said impedance reflection means comprises means for electrically shorting said second inductive coil.

12. A communications link, as recited in claim 9, wherein said external receiver means further comprises:

means for coherently detecting said selectively amplitude modulated inductive field; and means for discriminating between said selectively amplitude modulated inductive field caused by said first subcarrier frequency and said second subcarrier frequency.

13. A communications link, as recited in claim 1, wherein said modulation means further includes means fon generating an amplitude modulated bit mark.

14. A communications link, as recited in claim 12, further comprising:

means for establishing frequency lock between said internal transmitter and said external receiver; and means for establishing bit phase lock between said internal transmitter and said external receiver.

15. A communications link, as recited in claim 14, further comprising a means for verifying the establishment of an inductive communications link comprising:

means for determining the existence of said frequency lock and said bit phase lock; and means for generating a signal indicating said frequency lock and said bit phase lock whereby said establishment of said inductive communications link is verified.

16. A communications link, as recited in claim 1, further comprising:

means for generating power in said internal receiver and said internal transmitter from said inductive field; and means for inhibiting said transmitting digitally formatted information to and from said programmable medical device until said generated power achieves a preselected value.

17. A communications link, as recited in claim 16, wherein said internal transmitter further comprises means for transmitting a status of said programmable medical device.

18. A communications link, as recited in claim 17, wherein said internal transmitter further includes means for transmitting stored data to said external receiver.

19. A communications link, as recited in claim 4, wherein said first counter is a ripple counter.

20. A communications link, as recited in claim 4, wherein said clock includes a tuning fork crystal for high precision.

* * * * *